United States Patent [19]

Cha

[11] Patent Number: 5,415,746

[45] Date of Patent: May 16, 1995

[54] POTENTIOMETRIC ION DETERMINATIONS USING ENHANCED SELECTIVITY ASYMMETRIC ION-SELECTIVE MEMBRANE

[75] Inventor: Geung Sig Cha, Seodaemun, Rep. of Korea

[73] Assignee: E. I. Du Pont de Nemours and Company, Wilmington, Del.

[21] Appl. No.: 156,180

[22] Filed: Nov. 22, 1993

Related U.S. Application Data

[63] Continuation-in-part of Ser. No. 994,234, Dec. 21, 1992.

[51] Int. Cl.⁶ ............................................. G01N 27/26
[52] U.S. Cl. ................................ 204/153.12; 204/418; 204/403
[58] Field of Search ..................... 204/153.12, 153.21, 204/403, 409, 416, 418, 419, 433, 435

[56] References Cited

U.S. PATENT DOCUMENTS

| | | | |
|---|---|---|---|
| 4,840,893 | 6/1989 | Hill et al. | 435/817 |
| 5,114,859 | 5/1992 | Kagenow | 204/418 |
| 5,228,973 | 7/1993 | Sekiguchi et al. | 204/435 |
| 5,236,570 | 8/1993 | Ma et al. | 204/403 |

OTHER PUBLICATIONS

Guen Sig Cha et al., Potentiometric Ion and Bio-Selective Electrodes Based on Asymmetric Cellulose Acetate Membranes, 1989, vol. 36, No. ½ pp. 271-278.

*Primary Examiner*—John Niebling
*Assistant Examiner*—Bruce F. Bell

[57] ABSTRACT

This invention relates to a process for performing enhanced selectivity potentiometric ion determinations using an asymmetric ion membrane electrode having an asymmetric membrane with a hydrophilic layer fused to an ion-selective layer.

27 Claims, 12 Drawing Sheets

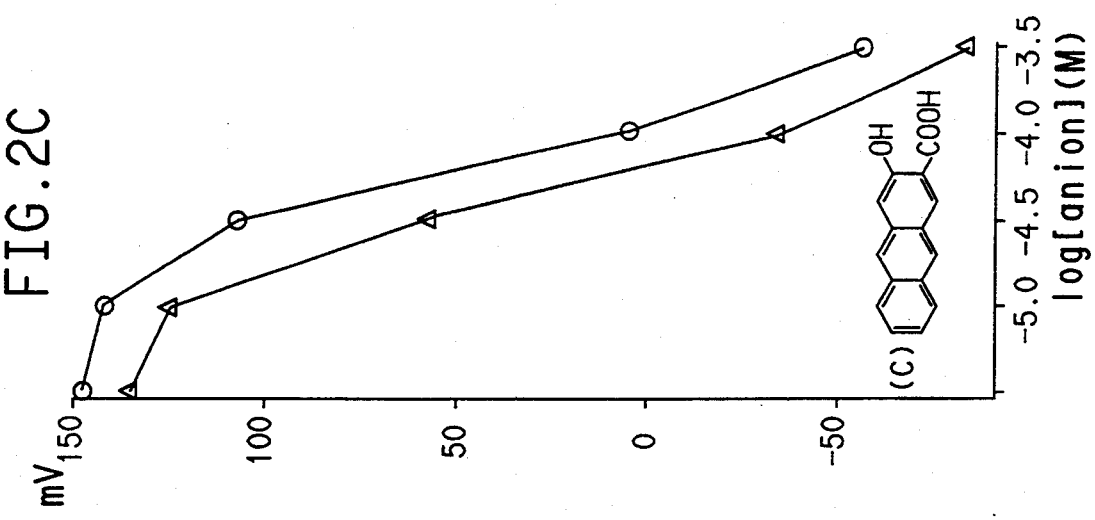
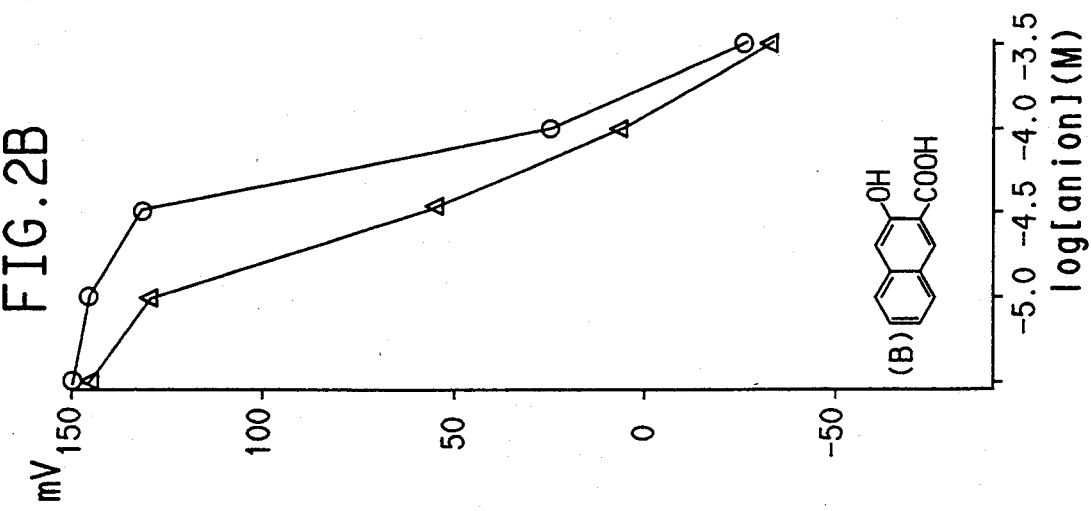
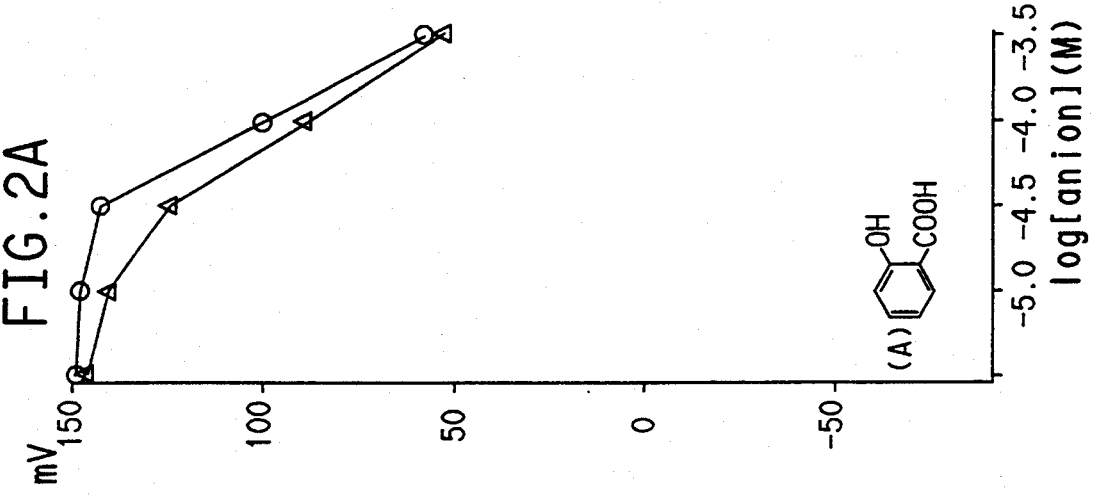

POTENTIOMETRIC ION DETERMINATIONS USING ENHANCED SELECTIVITY ASYMMETRIC ION-SELECTIVE MEMBRANE

CROSS-REFERENCE TO RELATED APPLICATION

This application is a continuation-in-part of U.S. Ser. No. 07/994,234, filed Dec. 21, 1992.

FIELD OF THE INVENTION

This invention relates to a process for performing potentiometric ion determinations and more particularly to a process for performing enhanced selectivity potentiometric determinations using asymmetric ion selective membranes.

BACKGROUND ART

Electrochemical measurements are widely used to determine the concentration of specific substances in fluids. These devices, referred to as ion-selective electrodes (ISEs), can be employed in a wide variety of potentiometric ion determinations, including, for example, the activity of fluoride ion in drinking water, the pH of process streams, and the determination of electrolytes in serum.

In the health care field, and in particular in the area of clinical diagnostics, ISEs are commonly used to measure the activity or concentration of various ions and metabolites present in blood plasma, serum and other biological fluids. For example, ISEs are typically used to determine $Na^+$, $Ca^{++}$, $Mg^{++}$, $K^+$, $Cl^-$, $Li^+$, pH, and carbon dioxide content in such fluids.

In general, conventional ISEs contain an ion-selective membrane, an internal filling solution or electrolyte, and an internal reference electrode. An external reference electrode used in conjunction with the ISE is typically a metal/metal halide electrode such as Ag/AgCl.

Conventional ISEs are typically bulky, expensive, difficult to clean and maintain, and tend to require an undesirably large volume of biological fluid. For these reasons, much attention has been directed towards developing more reliable ISEs of smaller size. These relatively small ISEs, referred to as ion-selective sensors or biosensors, can be inexpensively mass produced using techniques similar to those employed in the manufacture of electronic components, including for example, photolithography, screen printing, and ion-implantation. Ion-selective sensors and biosensors can be manufactured at much lower production cost than conventional ISEs, making it economically feasible to offer a single-use or limited-use disposable device, thereby eliminating the difficulty of cleaning and maintaining conventional ISEs. The reduced size of ion-selective sensors further serves to reduce the required volume of patient sample. Generally, a sensor can be either a miniature version of a conventional electrode or a device constructed using one or more of the above mentioned techniques. Maximum accuracy of the analytical or diagnostic result is obtained when the sensor responds only to the concentration or activity of the component of interest and has a response independent of the presence of interfering ions and/or underlying membrane matrix effects. The desired selectivity is often achieved by an ion-selective membrane containing an ion selective agent such as an ionophore. Generally, ion-selective membranes are formed from a heavily plasticized polymer matrix, such as polyvinyl chloride, which contains the ionophore selective for the ion of interest. For example, the ionophore valinomycin has been incorporated into a layer of membrane selective for potassium ions and trifluoroacetyl-p-butylbenzene or other trifluoroacetophenone derivatives has been used as ionophores selective for carbonate ions.

Determination of the concentration or activity of ionic species is achieved by measuring the EMF (electrical potential difference between the internal and external reference electrode, the electrodes being electrolytically connected by means of the sample solution at zero or near zero current flow) using a high impedance volt-meter. The reference electrode is electrolytically connected to the sample solution, typically by means of a salt bridge.

The accurate and rapid determination of total carbon dioxide species in physiological, industrial and environmental samples present a formidable challenge. Automated clinical analyzers are now routinely used for the determination of total carbon dioxide in biological samples using carbonate ion-selective electrodes or gas sensing electrodes configured as flow through detectors. However, none of the known carbonate selective membrane electrodes offer sufficient specificity or selectivity for unambiguous determination of carbonate ion. This is because ion-selective sensors utilizing carbonate selective ionophores are susceptible to interfering effects from comparatively large, hydrophobic ions such as perchlorate, gentisate, salicylate, p-amino salicylate and even larger species, such as heparin. Such salicylate ions are commonly present in physiological samples taken from patients treated with common analgesics.

Niedrach, U.S. Pat. No. 3,898,147, issued Aug. 5 1975, discloses a carbonate ion selective electrode having a hydrogen ion permeable membrane which consists of a hydrophobic elastomer. Measurement of pH of an aqueous electrolyte solution within the hydrogen ion permeable membrane serves as an indirect measurement of bicarbonate. However, this approach assumes absorption of carbon dioxide is the only source of hydrogen ions in the sample. Further, this system is susceptible to interferences from other endogenous acids.

Chapoteau, U.S. Pat. No. 4,810,351, issued Mar. 7, 1989, discloses a carbonate ion-selective membrane and electrode utilizing an ionophore consisting of an alkyl substituted fluoroacetophenone. High alkyl substitution of the ionophore is suggested to reduce drift in the electrode response in very fast flow situations. Further, the addition of a hydrophobic molecule to the ion selective membrane formulation is suggested to provide for the improved exclusion of interfering anions by repelling charged species from the solution phase. A C7-C9 quaternary ammonium surfactant is disclosed for binding the carbonate ions.

Kim et al., U.S. Pat. No. 4,272,328, issued Jun. 9, 1981, disclose an ion selective electrode multilayer analytical element which includes an ionophore containing membrane and a buffer zone in an amount sufficient to control the pH of the solution analyzed between about 7.5 to about 9.5. Under these conditions, it is suggested the element is comparatively less sensitive to the interfering effects of gentisate, salicylate and p-amino salicylate. Elimination of interferences from other large anions, such as, heparin and/or endogenous fatty acids is not mentioned.

Kim, U.S. Pat. No. 4,199,411, issued Apr. 22, 1980, discloses the structure of a halide ion-selective device having an overcoat made of a cellulose ester containing a polyol of from about 2 to about 6 hydroxyl groups. When added to the cellulose ester overcoat it was found the polyol "did not adversely affect the interference inhibiting characteristics of the cellulose ester layer". Hydrolysed cellulose acetate butyrate having from 6.4 to about 8.3 percent hydroxyl 0 groups is disclosed as one example of a cellulose ester. Kim does not mention or suggest the use of an asymmetric membrane or layers.

Anonymously, Research Disclosure 18730, November 1979 discloses the construction of halide ion-selective devices and the use of a halide-permeable overlayer comprising a cellulose ester to improve shelf life of the device. There is no mention or suggestion of an asymmetric membrane electrode.

Detwiler et al., U.S. Pat. No. 4,505,801, issued Mar. 19, 1985, disclose an overcoat layer for an ion-selective membrane, the overcoat layer having high selectivity for carbonate ions over potentially interfering ions, such as, salicylate, particularly at high salicylate concentrations. The disclosed overcoat layer has a discontinuous hydrophobic solvent dispersed within a continuous hydrophilic binder, a complexing agent for extracting oleophilic anions, a buffer which provides a pH in the range 7.5 to about 9.5 and a nucleating agent.

Ishizuka et al, U.S. Statutory Invention Registration No. H745, published Feb. 6, 1990, disclose the use of a buffered hydrophilic polymer binder layer laminated to a carbonate ion-selective layer for the purpose of eliminating or reducing interferences from salicylate, p-aminosalicylate and gentisate.

Cha et al., "Potentiometric Ion- and Bio Selective Electrodes Based On Asymmetric Cellulose Acetate Membranes", Talanta, vol. 36, pp. 271–278, (1989) disclose a bioselective electrode consisting of a cellulose triacetate membrane having a hydrolyzed first layer fused to a second layer, the second layer containing a neutral carrier and plasticizer, and an enzyme covalently attached to the exposed hydrolyzed surface of the first layer. The potentiometric response of trifluoroacetyl-p-butylbenzene (TFABB)-doped asymmetric cellulose acetate membranes to carbonate and other anions is disclosed (FIG. 4 of Cha). It is further disclosed the "asymmetric modification (to form hydroxyl groups) had little or no effect on the response characteristics of the membrane. The response slope and selectivity (or lack of it with respect to salicylate) observed are essentially the same as those found for PVC based membranes previously reported by Greenberg and Meyerhoff."

The asymmetric membranes disclosed by Cha et al. were developed for biosensor applications. Cha et al. do not mention or suggest an enhanced selectivity process for potentiometric determinations. Further Cha et al. do not mention or suggest a process for potentiometric ion determinations in which an asymmetric membrane electrode provides for reduced interference from salicylate or such a process in which the activity of the ion of interest is determined kinetically in order to achieve enhanced selectivity, as opposed to statically (at equilibrium).

BRIEF DESCRIPTION OF THE FIGURES

FIG. 2A depicts the potentiometric response of TFABB-doped unmodified CTA (_) and asymmetric CTA (o) membrane electrodes to the hydrophobic anion (A): salicylic acid. Potential measurements were made in a solution of 0.1M Tris-$H_2SO_4$, at pH 8.6.

FIG. 2B depicts the potentiometric response of TFABB-doped unmodified CTA (_) and asymmetric CTA (o) membrane electrodes to the hydrophobic anion:(B): 3-hydroxy-2-naphthoic acid. Potential measurements were made in a solution of 0.1M Tris-$H_2SO_4$, at pH 8.6. FIG. 2C depicts the potentiometric response of TFABB-doped unmodified CTA (_) and asymmetric CTA (o) membrane electrodes to the hydrophobic anion (C): 3-hydroxy-2-anthracenecarboxylic acid. Potential measurements were made in a solution of 0.1M Tris-$H_2SO_4$, at pH 8.6.

SUMMARY OF THE INVENTION

Figure 1A:
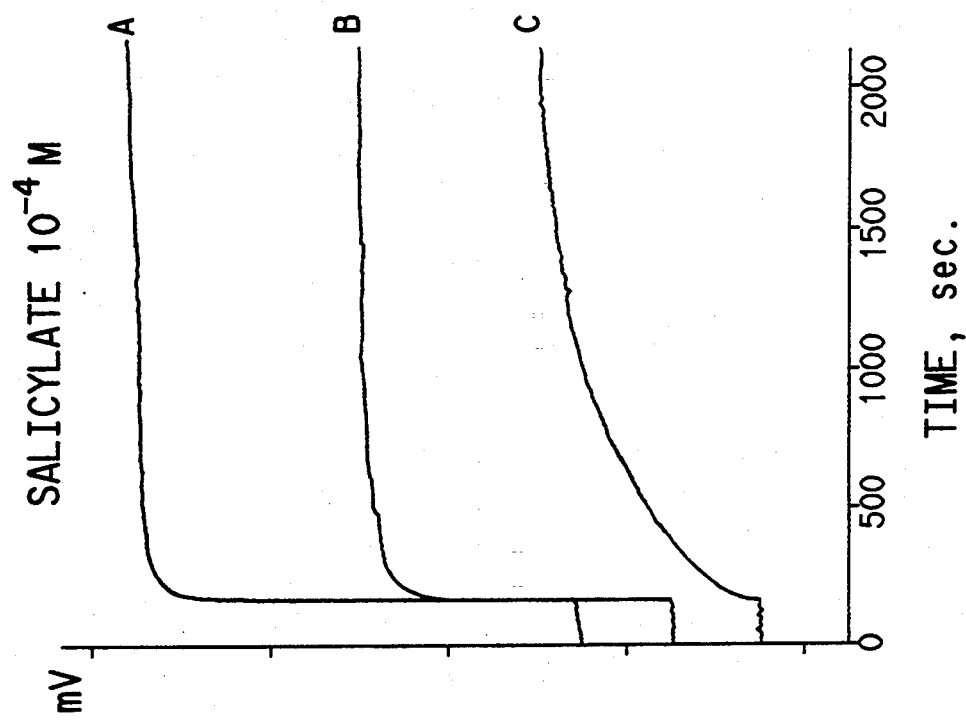
FIG. 1A depicts the dynamic response of carbonate ion-selective electrodes prepared with: (A): polyvinyl chloride (PVC), (B): unmodified cellulose triacetate (CTA), and (C): asymmetric CTA membranes subject to concentration changes of $10^{-5}$ to $10^{-4}$M (moles/liter) for salicylate.

This invention relates to a process for performing potentiometric ion determinations on biological samples using an ion selective asymmetric membrane electrode and a reference electrode electrolytically connected to the ion-selective asymmetric membrane electrode which comprises:

(a) contacting a biological sample suspected of containing an ion of interest with the ion-selective asymmetric membrane electrode, the ion-selective asymmetric membrane electrode having an asymmetric membrane with an ion selective layer and a hydrophilic layer fused to the ion-selective layer, the ionselective layer containing an ion-selective agent and a plasticizing agent, the hydrophilic layer being in contact with the sample, (b) measuring the potential difference between the ion-selective asymmetric membrane electrode and the reference electrode; and (c) relating the potential difference to the concentration of the ion of interest in the sample, thereby enhancing potentiometric ion selectivity.

Another aspect of the invention relates to a process for performing potentiometric carbonate ion determinations on biological samples using an ion selective asymmetric membrane electrode and a reference electrode electrolytically connected to the ion-selective asymmetric membrane electrode which comprises:

(a) diluting a biological sample suspected of containing carbonate ion and containing an interfering substance with a sufficient amount of a buffer solution such that the concentration of the interfering substance is less than about $2 \times 10^{-3}$M and the pH of the diluted sample is about 7.5 to 9.5;

(b) contacting the diluted sample with the ion-selective asymmetric membrane electrode having an asymmetric membrane with an ion selective layer and a hydrophilic layer fused to the ion-selective layer, the ion-selective layer containing an ion-selective agent and a plasticizing agent, the hydrophilic layer being in contact with the diluted sample, (c) measuring the potential difference between the ion-selective asymmetric membrane electrode and the reference electrode;

(d) relating the potential difference to the concentration of the carbonate ion in the sample, thereby enhancing potentiometric ion selectivity.

DETAILED DESCRIPTION OF THE INVENTION

This invention relates to a process for performing potentiometric ion determinations on biological samples using an ion selective asymmetric membrane electrode and a reference electrode electrolytically connected to the ion-selective asymmetric membrane electrode. The process comprises contacting a biological sample suspected of containing an ion of interest with the ion-selective asymmetric membrane electrode, the ion-selective asymmetric membrane electrode having an asymmetric membrane with an ion selective layer and a hydrophilic layer fused to the ion-selective layer, the ion-selective layer containing an ion-selective agent and a plasticizing agent, the hydrophilic layer being in contact with the sample, measuring the potential difference between the ion-selective asymmetric membrane electrode and the reference electrode; and relating the potential difference to the concentration of the ion of interest in the sample, thereby enhancing potentiometric ion selectivity.

By "ion-selective electrode (ISE)" is meant a potentiometric electrochemical sensor, the potential of which is related to the activity of an ion of interest in a sample. Generally, the potential is linearly dependent on the logarithm of the activity of the ion of interest. The activity of an ion of interest is defined as its concentration multiplied by an activity coefficient, where the activity coefficient is generally known or available in the art.

By "biological sample" is meant any fluid of biological origin including fluids of biological origin which have been chemically and/or physically treated, diluted, or concentrated prior to analysis. Examples of biological samples include serum, urine, plasma, whole blood, cerebrospinal fluid, amniotic fluid, saliva and tears.

By "ion of interest" is meant any ion to be determined using the asymmetric membrane ISE of the present invention. Various ions of interest include but are not limited to carbonate ($CO_3^{2-}$), chloride ($Cl^-$), bromide ($Br^-$), and phosphate ($HPO_3^-$). $CO_3^{2-}$ is the preferred ion of interest. The process of the present invention is especially suited for the determination of small hydrophilic anions such as chloride.

A general discussion of the principles of potentiometric ion sensors is provided by Oesch et al., "Ion Selective Membranes for Clinical Use," Clinical Chemistry, Vol. 32, No. 8, pp. 1448-1459, (1986) the disclosure of which is hereby incorporated by reference. Known conventional ISEs are typically composed of an ion selective membrane, an internal filling solution, and an internal reference electrode. ISEs can be classified according to the nature of the membrane material, and include solid state membrane electrodes, glass membrane electrodes, liquid membrane electrodes having charged ion-selective agents, and neutral liquid membrane electrodes having membranes formed from an organic solution containing an electrically neutral, ion-selective agent such as an ionophore held in an inert polymer matrix.

An ISE in combination with a sample solution, such as a biological sample, and an external reference electrode comprise a potentiometric cell assembly, so that by selectively transferring the ion of interest from the sample solution to the membrane a potential difference is generated between the internal filling solution and the sample solution which can be mathematically related to the concentration or activity ratio of the ion of interest in the two solutions contacting the membrane. Under ideal selectivity conditions of the membrane for the ion of interest, the potential difference is a linear function of the logarithm of the activity ratio of the ion of interest in the two solutions contacting the membrane (Nernst equation). A semi-empirical extension of the Nernst Equation (Nikolskii Eisenmann equation) for EMF may be utilized for non-ideal conditions. By EMF is meant the electrical potential difference between the internal and external reference electrode, the electrodes being electrolytically connected by means of the sample solution zero or near zero current flow.

The ISE utilized in the present invention is an enhanced selectivity asymmetric membrane electrode. The asymmetric membrane comprises a hydrophilic layer fused to an ion-selective layer.

The hydrophilic layer of the enhanced selectivity asymmetric membrane is a thin layer of polymer having a hydrophilic side. A variety of polymers can be utilized including but not limited to cellulose, cellulose ester, poly(vinyl acetate), polyurethane, poly(vinyl butyral), and copolymers of vinyl chloride. By "cellulose ester" is meant all ester derivatives of cellulose including but not limited to cellulose acetate, cellulose butyrate, and other members of a homologous series. By "poly(vinyl butyral)" is meant a copolymer of vinyl butyral, vinyl alcohol, and vinyl acetate. Examples of suitable polyurethanes include aliphatic, aromatic, and segmented polyurethanes.

The hydrophilic layer and ion selective layer of the asymmetric membrane are formed by fusing a polymeric membrane containing an ion selective agent and a placticizing agent to another polymer membrane having a hydrophilic side.

The polymeric membrane having a hydrophilic side can be prepared by dissolving the polymer in an amount of solvent, or mixture of different solvents, sufficient to dissolve the polymer, casting the dissolved polymer onto a plate or other surface, and allowing the solvent to evaporate. The amount of polymer used should be sufficient so as to produce a membrane of suitable thickness and structural integrity to withstand the hydrolysis of one of its sides and subsequent fusion to the polymer layer containing the ion selective agent and the plasticizing agent. The thickness of the resulting polymer layer can be from about $1\mu$ to about $1000\mu$ in thickness and is preferably about $50\mu$ in thickness.

The hydrolysis of one side of the polymer membrane can be achieved by subjecting it to a hydrolyzing agent to produce a hydrophilic surface composed of hydrophilic functional groups such as —OH, —$NH_2$, or —COOH. For example the hydrolysis can be easily achieved by floating the sample side (unmodified) of the polymer membrane on the liquid hydrolyzing agent.

By "hydrolyzing agent" is meant any substance capable of reacting with the polymer layer to produce hydrophilic functional groups on one side of the membrane. Bases are examples of suitable hydrolyzing agents. A wide variety of bases including, but not limited to, NaOH can be used. The hydrolysis is allowed to proceed for a time sufficient to produce hydrophilic functional groups on one side of the layer such that the desired maximum selectivity of the asymmetric membrane is achieved (maximum response to the ion of interest and maximum reduction of response to the interfering substance), without destroying the structural integrity of the layer during the hydrolysis. Extended periods for hydrolysis may result in hydrolysis of the entire polymer layer and can result in subsequent difficulties in fusing with the polymer layer having the ion selective agent(s); such a problem may be overcome by employing thicker polymer layers or shorter reaction times. Optimized hydrolysis times for particular polymer layers can be determined by subjecting the polymer layers to hydrolysis for various time periods and comparing the responses of the membranes thus formed.

The reaction time for hydrolysis can vary from 30 minutes to several hours, preferably the reaction time is about three to ten hours.

The polymer layer having a hydrophilic side can then be dried in preparation for fusion to the ion-selective layer. The layer can be dried using any means which allows for the evaporation of solvent without destroying the structural integrity of the layer. Air drying at room temperature is preferred. The hydrolyzed side of the resulting polymer layer is that side of the ion-permeable layer subsequently placed in direct contact with the biological sample.

The preferred polymer layer having a hydrolyzed side is a cellulose triacetate membrane having a hydrophilic side composed of hydroxyl groups. The layer can be simply prepared by dissolving cellulose triacetate in a mixed solvent (methylene chloride and chloroform), casting the solution as a thin layer onto a flat surface (to produce a layer of about 50μ thickness), and allowing the solvent to evaporate on standing. The cellulose triacetate layer can then be floated on a solution of NaOH for a sufficient period of time of around 4–10 hours, washed with water, and air-dried.

A polymer layer containing an ion selective agent(s) and a plasticizing agent is then fused with the polymer layer having a hydrophilic side. First, a solvent is added to the non-hydrophilic side of the polymer layer having a hydrophilic side in an amount sufficient to soften or swell the polymer layer without completely dissolving the layer or destroying its structural integrity by disrupting the hydrophilic side.

By "fusion" is meant a process whereby a mixture of a polymer, an ion-selective agent, and a plasticizing agent is cast onto the side of the polymer layer other than the side having the hydrophilic surface, and the solvent allowed to evaporate. The hydrophilic side of the polymer layer is immiscible with the plasticizing agent in which the ion-selective agent is dissolved. The ion selective agent(s) present in the cast solution diffuses into and mixes with the polymer matrix of the layer onto which it is cast and stops upon reaching the hydrophilic side of the layer.

The amount of polymer used in preparing the ion selective membrane should be sufficient so as to produce a membrane of suitable thickness and structural integrity to withstand the hydrolysis of one of its sides and subsequent fusion to the polymer layer containing the ion selective agent and the plasticizing agent. The thickness of the resulting polymer layer can be from about 1μ to about 1000μ in thickness and is preferably about 100μ in thickness.

The resulting asymmetric membrane consists of two fused layers, the hydrophilic layer, and the ion-selective layer. The hydrophilic layer, upon forming after fusion is preferably about 10μ in thickness.

Figure 7:
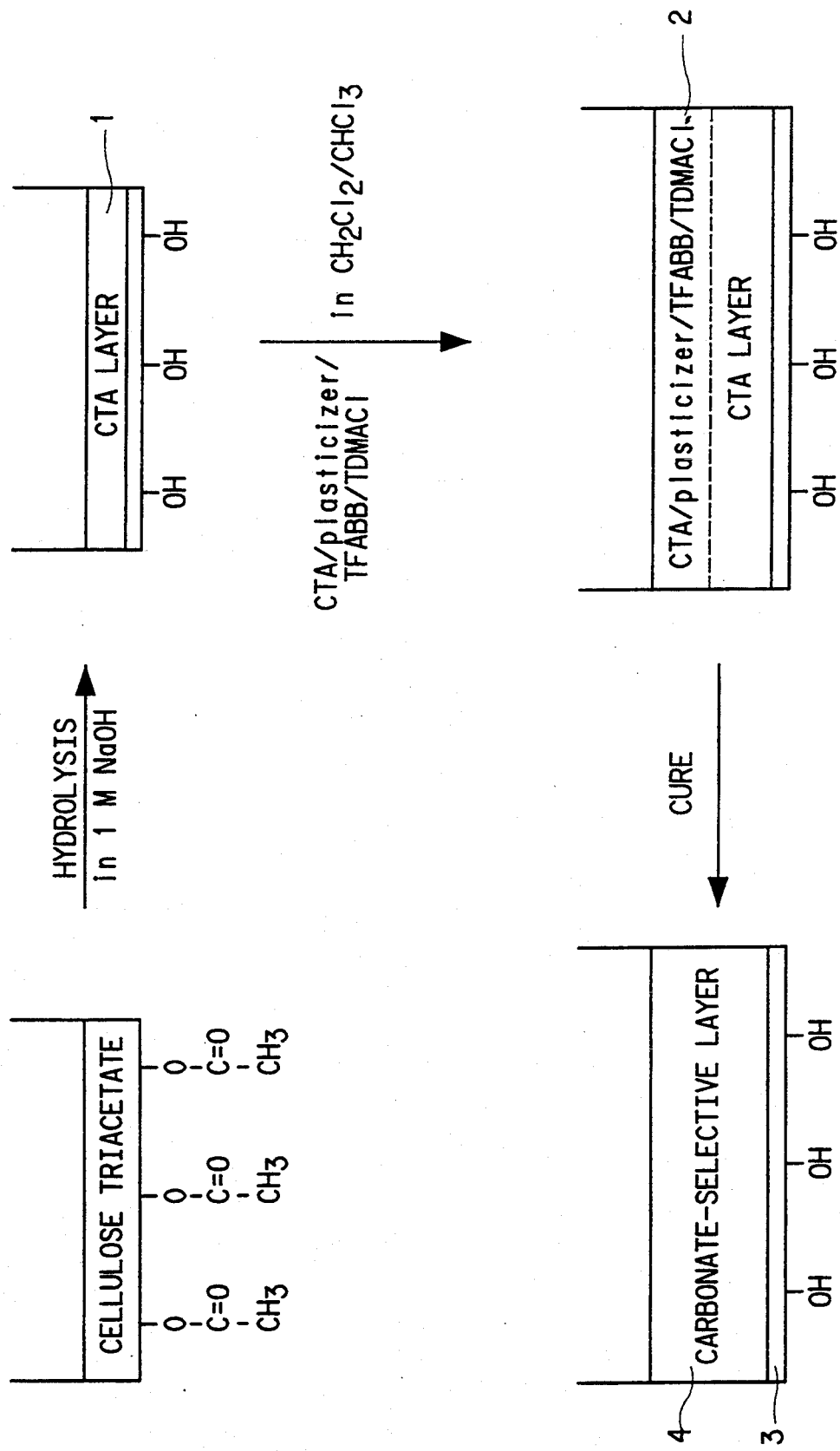
FIG. 7 schematically depicts preparation of an asymmetric carbonate ion selective membrane comprising an asymmetric membrane having a hydrophilic layer fused to an ion-selective layer.

This process is depicted schematically for the preparation of an asymmetric carbonate ion membrane in FIG. 7. Initially a polymer layer having a hydrophilic side (1) is prepared using the procedure described above. Then a second polymer layer (2) containing ion selective agents (TFABB as an ionophore and TDMAC as an ion complexing agent) is cast onto the first polymer layer. Diffusion or mixing of the ion selective agents into the first polymer layer occurs (across dotted line in FIG. 7) to produce an asymmetric membrane having a hydrophilic layer (3) and an ion selective (4) layer.

Alternatively, the polymer layer containing the ion-selective agent(s) can be prepared first, and the polymer layer having a hydrophilic layer subsequently fused to the ion-selective layer This mode of preparation is especially suited for use in a solid state planar sensor ISE format.

The use of an asymmetric membrane in the present invention is significant in that the fused layers allow for the incorporation of both an ion selective agent and a hydrophilic layer in a given ion selective membrane electrode. Direct hydrolysis of a membrane containing an ion selective agent does not appear to produce a membrane having the enhanced selectivity characteristics of the asymmetric membrane of the present invention. Further, the relatively slow response of an asymmetric CTA membrane in comparison with non-asymmetric membranes (as described in the Examples) towards large, hydrophobic anions may be due to the presence of the hydrophilic layer of the asymmetric membrane. Differences in response with respect to an asymmetric carbonate ion selective membrane may be further explained in terms of differences in the transport rate across the hydrophilic layer resulting from to the rapid reaction of the hydration sphere of the carbonate ion relative to that of a slower, less hydrophilic ion such as salicylate.

A variety of polymers can be used in preparing the ion-selective layer, included but not limited to those utilized to prepare the hydrophilic layer. Either the same or a different polymer can be utilized in preparing the hydrophilic layer and ion-selective layers of a particular asymmetric membrane. Use of the same polymer, such as cellulose triacetate for both the ion-permeable and ion-selective layer of a particular asymmetric membrane is preferred.

By "plasticizing agent" is meant any substantially water immiscible organic solvent which serves to solvate (plasticize) the polymer utilized in preparing the ion-selective layer. Further, the plasticizing agent is utilized to dissolve the ion-selective agent(s) prior to casting of the ion-selective layer onto the ion-permeable layer. A variety of plasticizing agents can be utilized in the present invention, including, but not limited to bis(2-ethylhexyl)sebacate (DOS), bis(2-ethylhexyl)adipate (DOA), bis(2-ethylhexyl)phthalate, dicapryl adipate, dipentylphthalate (DPP), dibutylsebacate, and 2-nitrophenyloctyl ether.

The amount of plasticizing agent used is that amount sufficient to maintain a solvated ion-selective membrane without destroying the selectivity or structural integrity of the membrane. The amount of plasticizing agent can vary from about 45 to about 75 weight %. Preferably a concentration of 65 weight % plasticizing agent is preferred.

By "ion-selective agent" is meant any substance or combination of substances which provides for the ion-selectivity of the non-selective layer. Suitable ion-selective agents include neutral ionophores and/or charged ion complexing agents..One or more ion selective agent(s) can be utilized in the same asymmetric membrane. Thus, an ion selective agent can include one or more ionophores, one or more ion-complexing agents, or any combination thereof (such as an ionophore and an ion complexing agent)..

Several ionophores can be utilized, including but not limited to trifluoroacetophenone derivatives. By "trifluoroacetophenone derivatives" is meant any derivative of trifluoroacetophenone, including, for example, trifluoroacetyl-p-butylbenzene (TFABB), trifluoroacetyl-p-decylbenzene, and trifluoroacetyl-p-dodecylbenzene.

The amount of ionophore used is that amount sufficient to provide for the maximum selectivity of the membrane without altering or destroying the structural integrity of the membrane..The amount of ionophore can vary from about 0.01 to about 65 weight % Preferably a concentration of 1 weight % ion selective agent is preferred.

By "ion-complexing agent" is meant any substance capable of forming a complex with the ion of interest, wherein the formation of the complex is attributable to differences in charge between the ion of interest and the ion complexing agent. Thus the ion-complexing agent is a charged entity. Suitable ion-complexing agents include, but are not limited to various quaternary ammonium salts. Examples of other ion-complexing agents include tridodecylmethylammonium chloride (TDMAC), methyltricaprylammonium chloride, tetraoctylammonium bromide, and methyltriodadecylammonium bromide. TDMAC is preferred for use in an asymmetric membrane carbonate ISE.

Other examples of ionophores suitable for use in the present invention include metalloporphyrins such as chloro(5,10,15,20-tetraphenylporphyrinato) manganese (III) (Mn[TPP]Cl and chloro(octaethylporphyrinato)indium (III) (In[OEP]Cl))

The amount of ion complexing agent used is that amount sufficient to provide for the maximum selectivity of the membrane without altering or destroying the structural integrity of the membrane. The amount of ion complexing agent can vary from about 0.1 to about 5 weight %. Preferably a concentration of 0.5 weight % ion selective agent is preferred.

The asymmetric ion-selective membrane electrode of the present invention comprises an asymmetric membrane and a conductor. By "conductor" is meant any electrically conductive substance which is in contact with the ion-selective layer of the asymmetric membrane. Examples of suitable conductors include metal/metal salts, metals, and carbon. By contact is meant either direct or indirect contact. By indirect contact is meant the addition of an electrolyte (typically as an electrolyte layer) between the ion selective layer of the asymmetric membrane and an internal reference electrode. For example, in a conventional ISE the conductor can be an internal reference electrode such as a metal/metal halide electrode (for example, an Ag/AgCl electrode) which is in indirect contact with the ion-selective layer of the asymmetric membrane by means of an electrolyte solution which serves as the internal filing solution. The electrolyte contains a common anion with the metal salt and must be of sufficiently high concentration to provide for low resistance and stable potential. Examples of suitable internal filing solution for use with conventional carbonate ISEs include but are not limited to $NaH_2PO_4$, and an aqueous mixture of $NaH_2PO_4$ and NaCl.

Figure 8A:
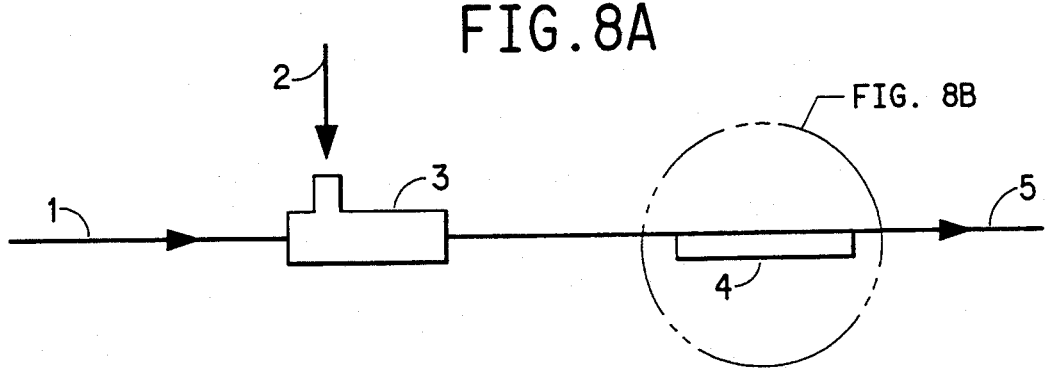
FIG. 8A schematically depicts a solid state planar sensor format for an asymmetric ISE.
Figure 8B:
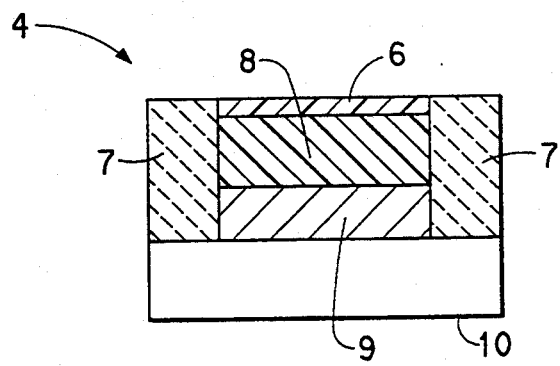
FIG. 8B schematically depicts the hydrophilic and ionselective layers of an asymmetric ISE in a solid state planar sensor format.

Alternatively, the asymmetric membrane can be utilized in a solid-state planar sensor electrode format in which case the electrolyte may or may not be utilized between the conductor and the asymmetric membrane. Solid state ion sensors are typically made by casting polymeric membranes directly on a solid surface, such as a metal conductor. FIG. 8A depicts schematically a solid-state planar sensor format having an asymmetric membrane ISE. The sample solution (1) is diluted with a buffer (2) and mixed using any suitable mixing device (3), such as an in-line mixer (for example, a spinning shaft) or an elastomeric element with mutating fingers for mixing. The mixed solution is then contacted with the asymmetric membrane ISE (4), the response determined by measuring the difference in potential between a reference electrode in contact with the sample and the carbonate ion selective electrode, and the remaining waste (5) solution discarded. The asymmetric membrane (FIG. 8B), having a hydrophilic layer (6) and an ion selective layer (8) is directly in contact with a conductor (9), the membrane being enclosed at least partially by a dielectric material (non-conducting substance) such as ceramic or glass. The asymmetric ISE is placed on a suitable substrate (10).

By "reference electrode" is meant any suitable external reference electrode, such as a metal/metal halide electrode. The reference electrode maintains a virtually invariant potential under the conditions prevailing in an electrochemical measurement and serves to permit the observation, measurement, or control of the potential of the asymmetric membrane electrode. For example, an Orion sleeve-type double junction Ag/AgCl electrode (Model 90-02) can be utilized as a reference electrode. The reference electrode is electrolytically connected (such as through a salt bridge) to the sample which is in contact with the asymmetric membrane such that the potential difference between the ion-selective asymmetric membrane electrode and the reference electrode can be measured. The electrodes can be connected through a high impedance amplifier or by any means capable of measuring a potential difference.

The potential difference or EMF can be determined either through static measurements or through kinetic measurements.

Static mode potentiometric measurements can be obtained by allowing the sample and electrolyte solutions to achieve their steady-state equilibrium or near equilibrium potentials prior to potential difference measurement. Such measurements can be made using well-known procedures and equipment.

Kinetic measurements, which are preferred, can be obtained by measuring the potential difference with time, prior to equilibrium in a static mode measurement, or by measurements performed in flow injection analysis studies. Such kinetic measurements can be performed using a flow through detector which is fitted to an electrode body, such a a Phillips electrode body; (IS-561), Glosblaserei Moller, Zurich). A kinetic measurement can be performed using such a flow through detector in conjunction with a standard metal/metal halide reference electrode (such as AG/AgCl), an ion sensing electrode having an asymmetric membrane, and a suitable sample flow loop system (as described in the Examples). The EMF or potential difference values can be recorded with time using a high impedance amplifier/analog-to-digital converter.

One of the important features of the present invention is the ability to perform enhanced selectivity potentiometric ion determinations by reducing the undesirable effects caused by various interfering substances.

By "interfering substance" is meant any substance other than the ion of interest, whose presence in the biological sample affects the measured potential of an ISE for a particular ion of interest. Such interfering substances can result in incorrect potential difference or EMF determinations, such as falsely elevated or falsely depressed activities or concentrations for the ion of interest. Examples of interfering substances include but are not limited to salicylate or p-amino salicylate, other salicylate-like hydrophobic organic acids, and gentisate.

The preferred asymmetric membrane for use in the present invention is a carbonate ion-selective electrode consisting of a cellulose-triacetate hydrophilic layer composed of hydroxyl groups, fused to a cellulose triacetate ion-selective layer having TFABB as the ion-selective agent, DOA as the plasticizing agent and contains TDMAC as an ion-complexing agent.

The carbonate species ($CO_3^{2-}$) is related to gaseous $CO_2$ by the following equilibrium relationships:

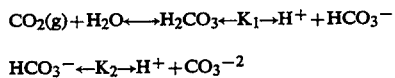

$$CO_2(g) + H_2O \leftrightarrow H_2CO_3 \leftarrow K_1 \rightarrow H^+ + HCO_3^-$$

$$HCO_3^- \leftarrow K_2 \rightarrow H^+ + CO_3^{-2}$$

where $K_1$ and $K_2$ are the dissociation constants and $K_1 = 4.3 \times 10^{-7}$ and $K_2 = 4.8 \times 10^{-11}$ at 25° C.

At normal serum pH of 7.0 to 7.5, the majority of the species are in the bicarbonate form. By shifting the pH to a more alkaline pH of about 8.5 to 8.7, a siginficantly higher proportion of the species present will be in the carbonate ($CO_3^{-2}$) form.

The carbonate asymmetric membrane responds to $CO_3^{-2}$ because of the TFABB as a result of the carbonate species forming a 1:1 or a 2:1 adduct with the ionophore TFABB in the ion selective layer of the membrane This is disclosed by Meyerhoff et al., Role of Trifluoroacetophenone Solvents and Quaternary Ammonium Salts In Carbonate-Selective Liquid Membrane Electrodes", Analytical Chemistry, vol. 59, pp. 144-150, (1987). The structure of TFABB and the 1:1 and 2:1 adducts is shown below:

TFABB can be prepared using known procedures such as that described by Herman, H. B., et al., Preparation and Properties of a Carbonate Ion Selective Membrane and Electrode, Analytica Chimica Acta, vol. 76, pp. 155-164, the disclosure of which is hereby incorporated by reference. Alternatively, p-decyl-a,a,a-trifluoroacetophenone (Trans World Chemicals, Inc. Rockville, Md.), can be used in place of TFABB. Furthermore, any of several known derivatives of TFABB can be used as ionophores. Such known derivatives include those described by Behringer et al., Anion Selectivities of Trufluoroacetophenone Derivatives of Neutral Ionophores in Solvent-Polymeric Membranes, Analytica Chimica Acta, vol 233, pp. 41-47 (1990), the disclosure of which is hereby incorporated by reference.

A further example of an asymmetric membrane useful in the present invention is a chloride ion-selective membrane electrode consisting of a cellulose-triacetate hydrophilic layer composed of hydroxyl groups, fused to a cellulose triacetate ion-selective layer having a metalloporphyrin ion-selective agent, such as chloro (5,10,15,20-tetraphenylporphyrinato)manganese (III) (Mn[TPP]Cl) (available from Aldrich Chemical Co., Milwaukee, Wis.) or chloro(octaethylporphyrinato)indium (III) (In[OEP]Cl), In[OEP]Cl can be synthesized using known procedures (Bratti, M., et al., "Preparation of Indium (III) Tetraphenylporphine Complexes", Inorg. Nucl. Chem. Lett. vol. 8, pp. 133-137 (1972); octaethylporphyrin (Mid Century, Posen, Ill.) can be metallated with In (III) using known procedures).

The following examples serve to illustrate the present invention.

EXAMPLE 1

Preparation of An Asymmetric Cellulose Triacetate Carbonate Ion-Selective Membrane A thin cellulose triacetate membrane was prepared by dissolving 100 mg of cellulose triacetate (CTA), (Fluka Chemicals, Ronkonkoma, N.Y.) in 2.5 ml of a mixed, analytical-reagent grade, solvent containing 1.5 ml of methylene chloride (Junsei Chemical Co., Ltd, Tokyo, Japan) and 1.0 ml of chloroform (Junsei Chemical Co., Ltd, Tokyo, Japan). The solution was cast on a flat plate. Spreading of the solution was confined by a 36 mm inside diameter ring. The solvent was allowed to evaporate overnight leaving a membrane approximately 50 micrometers thick. The acetyl groups on the lower side of the membrane were hydrolyzed by floating the membrane on an excess of 1M sodium hydroxide (Junsei Chemical Co. Ltd.) solution at room temperature for 4.5 h. This resulted in a polymer layer having a thin hydrophilic, hydroxylated surface.. The membrane was washed by immersing it in 500 mlof distilled water. This process was repeated a second time to insure termination of they hydrolysis reaction and allowed to dry in air at room temperature. The dry membrane was placed on a second glass plate with the hydroxylated surface face down. A 22 mm inside diameter ring was placed on the upper surface of the membrane to confine the spreading of subsequent solutions. 1.2 ml of methylene chloride was applied to the membrane to soften or pretreat the upper surface for 30 min. During this period the membrane was kept inside a desiccator with its vacuum tap open to reduce the rate of evaporation of the methylene chloride. A solution of the components for the carbonate ion-selective membrane was prepared by dissolving 35 mg of CTA; 16.6 mg of the ionophore trifluoroacetyl-p-butylbenzene, TFABB, (Specialty Organics Inc., Irwindale, Calif.); 100 μl of the plasticizing agent, bis(2-ethylhexyl) sebacate (Fluka Chemicals, Ronkonkoma, N.Y.) and 2.0 mg of the ion complexing agent tridodecylmethylammonium chloride (Polysciences Inc., Warrington, Pa.) in a mixed solvent containing 0.8 ml of methylene chloride and 0.8 ml of chloroform. This solution was applied to the membrane area within the previously mentioned 22 mm diameter ring and allowed to evaporate overnight. Evaporation was controlled by keeping the membrane in a vacuum desiccator with the vacuum tap slightly open. In this manner the second membrane layer referred to as the ion-selective layer (containing the ionophore, plasticizing agent, and the ion complexing agent) was fused to the side of the polymer membrane other than the hydrophilic side to produce an asymmetric carbonate ion selective membrane.

EXAMPLE 2

Preparation of a Carbonate Ion-Selective Electrode with an Asymmetric Carbonate Ion Selective Membrane Electrochemical properties of the membranes were evaluated in conventional ion-selective electrode devices. Small, 5.5 mm diameter, disks were cut from the asymmetric carbonate ion selective membrane prepared as described in Example 1 and were tested using a Phillips electrode body (Glasblaserei Möller, Model IS-561, Zurich, CH). A disk was placed in an electrode bodie with the hydrophilic surface facing the outer sample solution (electrolyte). The internal filling solution employed contained 0.1M sodium dihydrogen phosphate; 0.1M disodium hydrogen phosphate and 0.01M sodium chloride. The conductor (internal reference electrode used was a standard Ag/AgCl electrode. The reference electrode used was a sleeve-type double junction silver/silver chloride electrode (Orion, Model 90-02). The potential of the carbonate ion-selective electrode was measured using a high input impedance electrometer connected to a Personal Computer (Young Sun Computer Co., Ltd., Seoul, Korea, Model compatible with an IBM at 286) equipped with an analog-to-digital converter or by using an electrode switch box (Fisher Accumet, Model 157; Romulus, Mich.) and a pH-millivolt meter (Fisher Accumet, Model 620) All of the data of FIGS. 1A and 1B and Tables 1 and 2 below was obtained using the electrode switch box (Fisher Accumet, Model 157; Romulus, Mich.) and a pH-millivolt meter (Fisher Accumet, Model 620) All of the data of FIGS. 1A and 1B and FIGS. 3 through 6 was obtained using a high input impedance electrometer connected to a Personal Computer (Young Sun Computer Co., Ltd., Seoul, Korea, Model compatible with an IBM at 286) equipped with an analog-to-digital converter The response and selectivity characteristics of the asymmetric membrane electrodes were evaluated by comparison with identical assemblies in which the asymmetric CTA membrane was replaced by an ion-selective layer prepared from either unmodified (not subject to hydrolysis) CTA or polyvinyl chloride, PVC. These membrane materials, prepared and testing using known procedures and techniques in preparation are disclosed by Cha, G. S. and Meyerhoff, M. E., "Potentiometric Ion- and Bio-Selective Electrodes Based on Asymmetric Cellulose Acetate Membranes" Talanta, vol. 36, pp. 271–278, (1989) the disclosure of which is hereby incorporated by reference.

EXAMPLE 3

Equilibrium Potentiometric Responses Using Static Mode Measurements

Potentiometric evaluation of the carbonate ionselective electrode with the asymmetric CTA membrane described in Example 2 was conducted using static mode measurements in which the potential difference between the electrolyte and the sample solution was allowed to reach equilibrium. Measurement of the electromotive force at 10 minutes after the standard addition of the respective salt was found to be equivalent to equilibrium. The equilibrium potentiometric response characteristics of the asymmetric CTA membrane were evaluated and compared with unmodified CTA membranes. These responses were obtained by adding standard solutions added to a stirred 200 ml volume of background electrolyte (0.1M 2-amino-2-hydroxymethyl-1,3-propanediol, TRIS-sulfuric acid mixture, pH 8.6). Measurements were taken at room temperature and the equilibrium measurements recorded. Table 1 provides selectivity coefficients calculated using the equilibrium response potential taken 10 minutes after the standard additions. The potentiometric selectivity coefficient, $k^{pot}_{CO_3^{2-},i}$, can be calculated by the following:

$$\log k^{pot}_{CO_3^{2-},i} = \frac{E_2 - E_1}{2.303\, RT/z_A F} + \frac{1 - (z_{CO_3^{2-}})(\log a_{CO_3^{2-}})}{(z_i)}$$

where:

$a_{CO_3^{2-}}$ is the activity of the carbonate ion.

$z_{CO_3^{2-}}$ is an integer with the sign and magnitude corresponding to the charge of the carbonate ion.

$z_i$ is an integer with the sign and magnitude corresponding to the charge of the interfering ion.

$E_1$ and $E_2$ are the experimentally observed potentials of the two separate solutions, one solution containing the carbonate ion at an activity $a_{CO_3^{2-}}$, the other containing the ion i at the same activity.

R is the gas constant and is equal to 8.31441 $JK^{-1}mol^{-1}$.

T is the thermodynamic temperature (in °K.).

F is the Faraday constant and is equal to $(9.648670\pm0.000054)\times10^4$ C $mol^{-1}$..

The results shown in Table 1, indicate that asymmetric modification of the instant invention had little or no effect on the response to small anions, such as carbonate, chloride, acetate and bromide.

However, the asymmetric carbonate ion selective membrane exhibited reduced responses towards larger anions, such as salicylate and perchlorate.

TABLE 1

Comparison of the Static Mode Potentiometric Selectivity Coefficients for TFABB-Doped Unmodified CTA (n-CTA) and Asymmetric CTA Membrane Electrodes (Asym-CTA)*

| matrix | $\log k^{pot}_{CO_3^{2-},j}$ | | | | | | |
|---|---|---|---|---|---|---|---|
| | Cl− | pyruvate | oxalacetate | NO$_3^-$ | I− | IO$_4^-$ | Salicylate |
| n-CTA | −2.54 | −0.48 | −0.49 | −0.33 | 0.43 | 1.93 | 2.04 |
| Asym-CTA | −2.52 | −1.54 | −1.54 | −0.36 | 0.43 | 2.76 | 1.72 |

*Evaluated in 0.1M Tris-H$_2$SO$_4$, pH 8.6. The separate solution method was used by employing concentrations instead of activities. The interfering anion, i, concentration was 0.01M except chloride (0.1M) and salicylate (3 × 10$^{-4}$ M).

EXAMPLE 4

Kinetic Potentiometric Responses

A. Dynamic Responses Using Static Mode Measurements

Figure 1B:
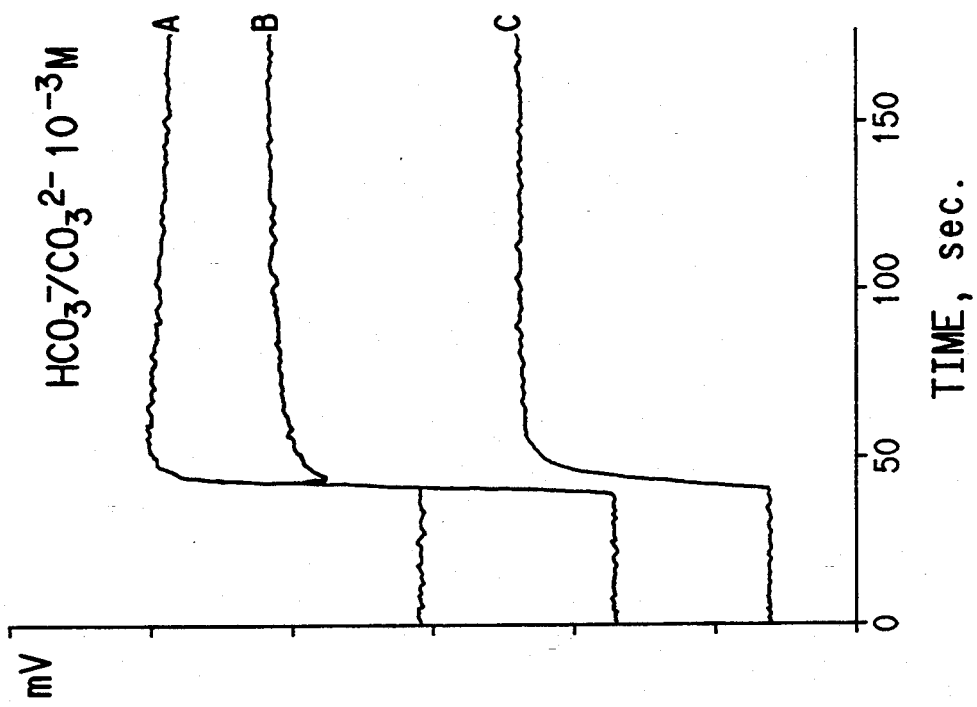
FIG. 1B depicts the dynamic response of carbonate ion-selective electrodes prepared with: (A): polyvinyl chloride (PVC), (B): unmodified cellulose triacetate (CTA), and (C): asymmetric CTA membranes subject to concentration changes of $10^{-4}$ to $10^{-3}$M for $CO_3^{2-}$.

Differences in the quantitative responses are enhanced by viewing the dynamic response curves of the electrodes to different ions using electrodes having either the conventional cellulose. This was done by recording the change of potential over time after addition of the standard solutions. FIGS. 1A and B compare the response of carbonate ion-selective electrodes incorporating three membranes. Including non-asymmetric polyvinyl chloride (PVC), non-asymmetric CTA, and asymmetric CTA carbonate ion selective membranes, to salicylate and carbonate ions.

FIGS. 1A and 1 B indicates all three electrodes showed a similarly fast response upon the addition of carbonate ion to the sample solution in the concentration range $10^{-4}$ to $10^{-3}$M. However, while the PVC and CTA membranes responded relatively fast to a salicylate concentration change, the asymmetric CTA membrane exhibited an extremely slow response when the salicylate concentration was changed from $10^{-5}$ to $10^{-4}$M. The response characteristics of the non asymmetric CTA membrane was very similar to the response of the non asymmetric PVC membrane. Both exhibited similar kinetic (dynamic) response towards both carbonate and salicylate ions. It is hypothesized the slow response of the asymmetric CTA membrane towards large, hydrophobic anions was due to the presence of the hydrophilic layer of the asymmetric membrane. It is speculated that differences in response are due to differences in the transport rate across the hydrophilic region due to the rapid reaction of the hydration sphere of the carbonate ion relative to that of a slower, less hydrophilic ion such as salicylate. Support for the above was obtained by repeating the experimental protocol described above with larger, even more hydrophobic analogues. Anions from 3-hydroxy-2-naphthoic acid and 3-hydroxy-2-anthranoic acid were compared to salicylate. EMF values were taken at 10 minutes after standard addition of the anions.

FIGS. 2A–C show the increased response with larger additions of the more hydrophobic anions. The asymmetric membrane exhibited consistently showed a reduced response characteristics toward these hydrophobic anions relative to the non asymmetric membrane. At higher concentrations of the hydrophobic anions, the asymmetric membranes achieved only a small degree of response reduction as compared with the non asymmetric CTA membranes. Table 2 shows the selectivity of both the non asymmetric CTA and asymmetric CTA membrane for carbonate relative to salicylate over a concentration range of $1 \times 10^{-5}$ to $1 \times 10^{-2}$M.

At lower salicylate concentrations, the asymmetric membrane achieved a greater degree of salicylate response reduction relative to the non-asymmetric CTA membrane.

TABLE 2

Static Mode Potentiometric Selectivity Coefficients Observed at Various Salicylate Concentrations for Unmodified CTA (non-CTA) and Asymmetric CTA Membrane Electrodes*

| | $\log k^{pot}$ $CO_3^{2-}$, Salicylate Interfering Salicylate Concentration, M | | | | | | |
|---|---|---|---|---|---|---|---|
| | $1 \times 10^{-5}$ | $3 \times 10^{-5}$ | $1 \times 10^{-4}$ | $3 \times 10^{-4}$ | $1 \times 10^{-3}$ | $3 \times 10^{-3}$ | $1 \times 10^{-2}$ |
| n-CTA | 0.57 | 0.97 | 1.56 | 2.04 | 2.71 | 3.18 | 3.73 |
| Asym-CTA | 0.18 | 0.30 | 0.58 | 1.72 | 2.43 | 3.00 | 3.58 |

*Evaluated in 0.1M Tris-H$_2$SO$_4$, pH 8.6. The separate solution-matched potential method was used by employing concentrations instead of activities.

B. Flow Injection Measurements

Figure 3:
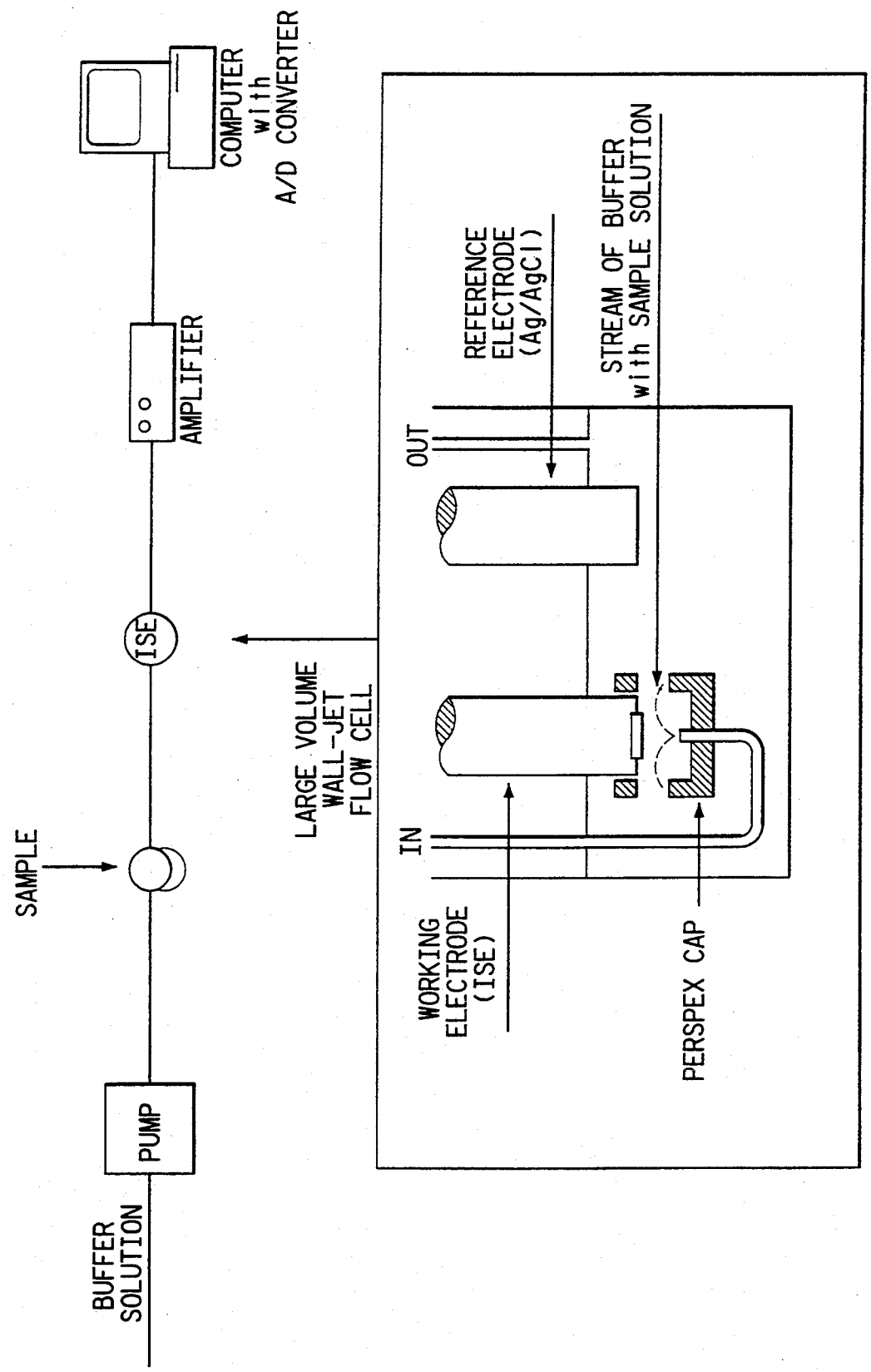
FIG. 3 is a schematic depiction of a membrane electrode-based flow injection analysis (FIA) system with a large volume wall-jet flow cell.

The arrangement shown in FIG. 3 was used to evaluate the performance of the asymmetric carbonate ion-selective membrane electrode in a flow injection analysis mode.

A Phillips electrode body was fitted with a special flow cap for use as a flow through detector in a large volume wall jet configuration. The construction of this flow through detector is described by Trojanowicz, M. and Meyerhoff, M. E., "Potentiometric pH Detection in Suppressed Ion Chromatography" Anal. Chem., vol. 91, 787-789.(1989), the disclosure of which is hereby incorporated by reference. An Orion silver/silver chloride reference electrode together with the working carbonate ion-selective electrode were placed in a large beaker containing the reagent buffer (0.1M TRIS-sulfuric acid, pH 8.6]. The four-way injection valve (Rheodyne, Model 7125) equipped with a sample loop of 150 μl was connected to the flow cap with a length of polytetrafluoroethylene (PTFE) tubing having an internal diameter of 0.30 mm. The buffer stream (0.1M Tris-sulfuric acid, pH 8.6) was pumped at a flow rate of 7.5 ml/min using a peristaltic pump (Ismatech, Model 7331-00, Zurich). Standard solutions of anions were prepared in the same buffer. Volumes of 150 μl were introduced for each test. All tests were performed at room temperature. EMF values were recorded every 0.1 second using a high impedance voltmeter equipped with an analog-to-digital converter as described earlier.

Figure 4A:
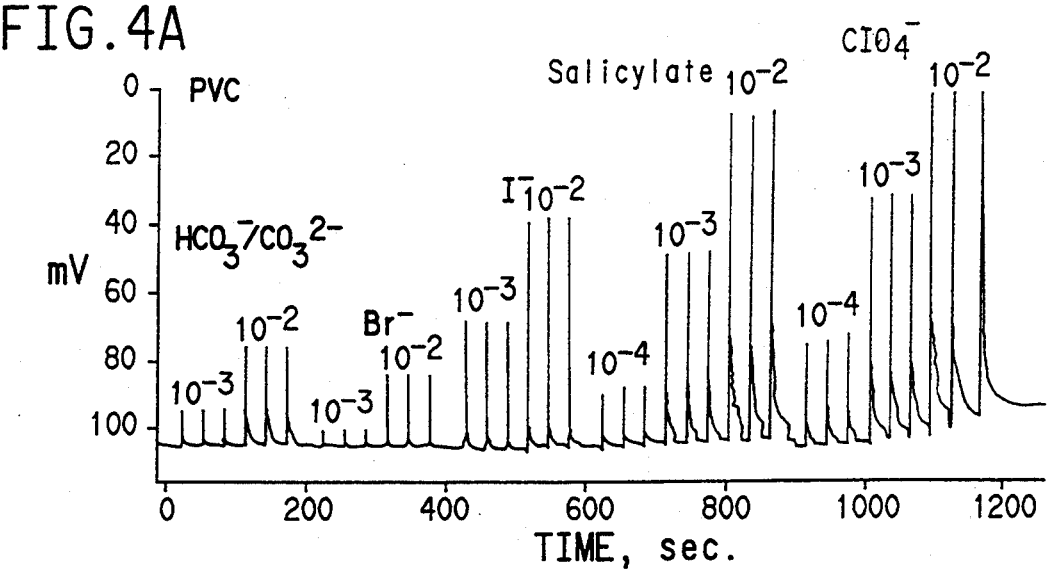
FIG. 4A depicts the potentiometric flow-injection anion response obtained with TFABB-doped carbonate-selective PVC membrane electrodes as flow-through detectors. Aliquots (150 µL) of anion standard solutions containing 0.1M Tris-$H_2SO_4$, pH 8.6 buffer, were injected into a background electrolyte stream containing 0.1M Tris-$H_2SO_4$, pH 8.6, at 7.5 mL/min.
Figure 4B:
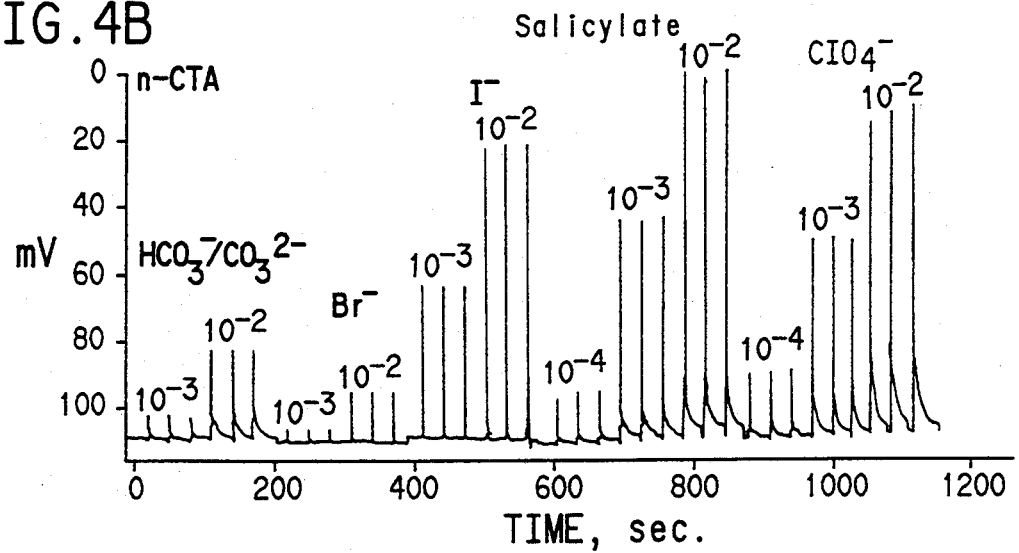
FIG. 4B depicts the potentiometric flow-injection anion response obtained with unmodified normal CTA membrane electrodes as flow-through detectors. Aliquots (150 µL) of anion standard solutions containing 0.1M Tris-$H_2SO_4$, pH 8.6 buffer, were injected into a background electrolyte stream containing 0.1M Tris-$H_2SO_4$, pH 8.6, at 7.5 mL/min.
Figure 4C:
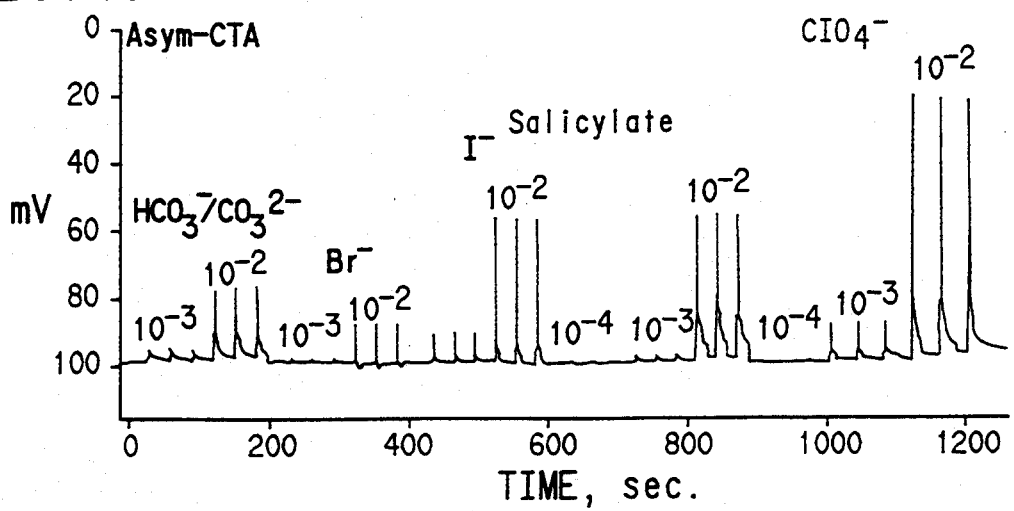
FIG. 4C depicts the potentiometric flow-injection anion response obtained with asymmetric CTA membrane electrodes as flow-through detectors. Aliquots (150 µL) of anion standard solutions containing 0.1M Tris-$H_2SO_4$, pH 8.6 buffer, were injected into a background electrolyte stream containing 0.1M Tris-$H_2SO_4$, pH 8.6, at 7.5 mL/min.

When the ion-selective electrode was employed directly in a wall-jet configuration, only a fraction of the response to the injected ions was observed because such flow injection systems operate in a nonequilibrium mode. The resulting response signals (peaks) depended on the dynamic response characteristics of the ion-selective detector used. FIGS. 4A-C provide a comparison of the potentiometric flow injection response to anions obtained using the PVC non-asymmetric, non-asymmetric CTA and asymmetric CTA membranes in electrodes.

A significantly reduced response of the asymmetric CTA membrane was observed for large, lipophilic anions, such as iodide, salicylate and perchlorate compared with the responses of the non asymmetric PVC and non-asymmetric CTA membranes. The non-asymmetric CTA membrane showed response characteristics practically the same as the non-asymmetric PVC membrane, indicating the reduced response of the asymmetric CTA membrane towards lipophilic anions is due to the presence of the modified hydrophilic surface on the ion-permeable layer.

In the static mode experiment of Example 3, the asymmetric CTA membrane and unmodified CTA membrane showed nearly the same equilibrium selectivity for carbonate and iodide. In contrast, the carbonate selectivity compared to that of iodide for CTA the asymmetric membrane was substantially improved in the flow injection detection system. The selectivity of the asymmetric membrane can therefore be most effectively enhanced by employing non-equilibrium flow through arrangements.

EXAMPLE 5

Measurement of Carbonate Ion in Serum Samples

SeraChem Level 1 Clinical Chemistry Control Human Serum-Assayed (Fisher Scientific, Orangeburg, N.J.). The effect of serum matrix on the carbonate response of the asymmetric carbonate ion-selective electrode was studied using a non asymmetric, PVC and asymmetric CTA membranes were prepared and used as described previously in Examples 1 to 3. The response of the electrodes was first tested with standards in aqueous solution and subsequently compared to the serum samples. Two milliliters of the aqueous standard or reconstituted serum sample were added to 18 ml of background electrolyte (0.1M TRIS-sulfuric acid, pH 8.6).

Figure 5A:
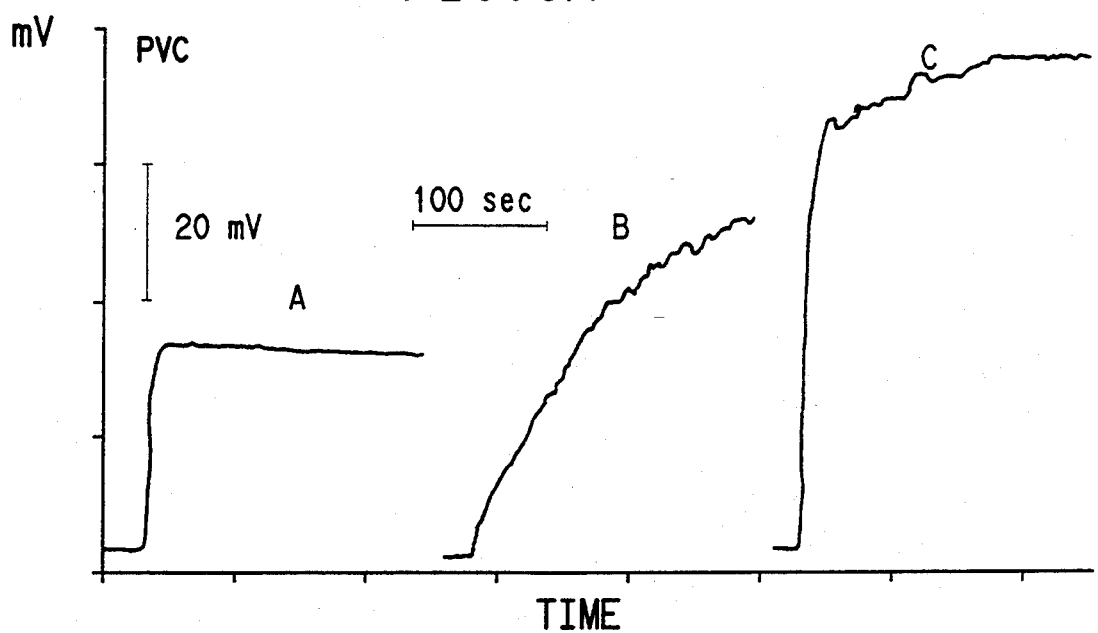
FIG. 5A depicts the dynamic response of the TFABB-doped PVC membrane electrodes to added standard solutions as follows: (A): 25 mM carbonate, (B): 1.0 mM salicylate, (C): a mixture containing 25 mM carbonate, 100 mM chloride, and 1.0 mM salicylate.. For each measurement, 2 ml of standard solutions were added to 18 ml of background electrolyte solutions containing 0.1M Tris-$H_2SO_4$ at pH 8.6.
Figure 5B:
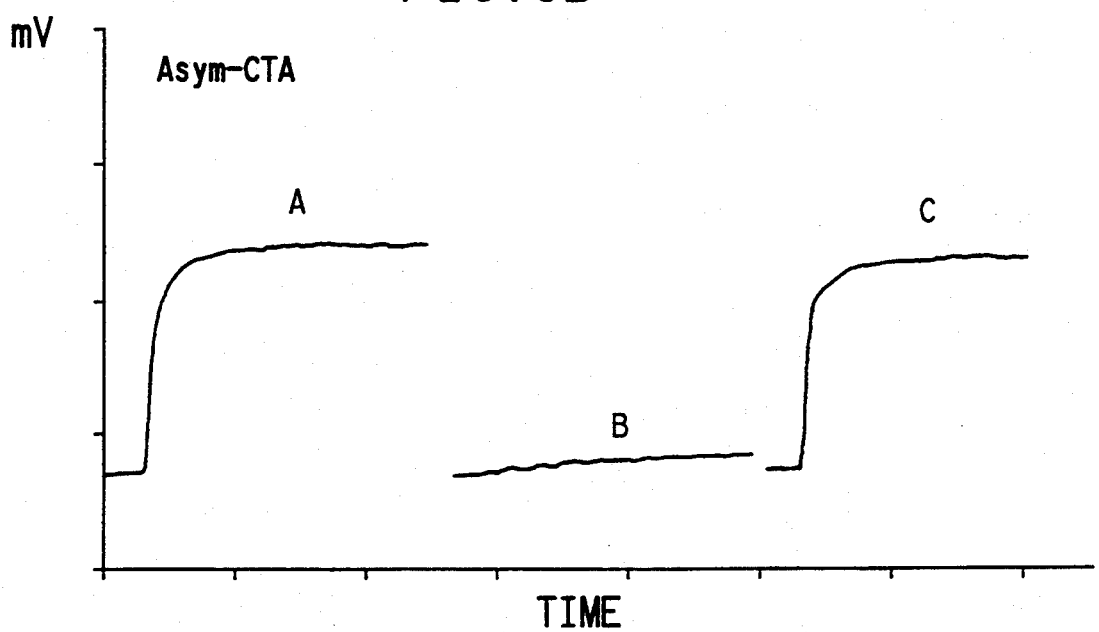
FIG. 5B depicts the dynamic response of the asymmetric CTA membrane electrodes to added standard solutions as follows: (A): 25 mM carbonate, (B): 1.0 mM salicylate, (C): a mixture containing 25 mM carbonate, 100 mM chloride, and 1.0 mM salicylate.. For each measurement, 2 ml of standard solutions were added to 18 ml of background electrolyte solutions containing 0.1M Tris-$H_2SO_4$, at pH 8.6.
Figure 6A:
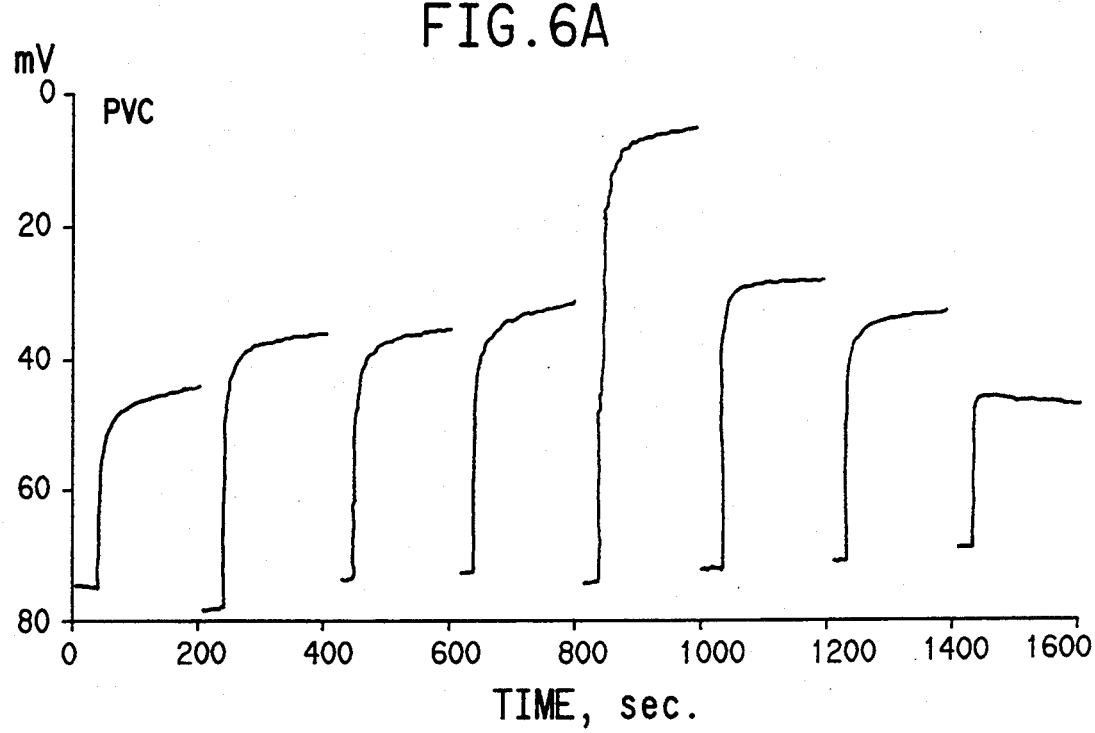
FIG. 6A depicts the potentiometric response of the PVC and asymmetric carbonate ion-selective membrane electrodes to added serum samples containing varying salicylate concentrations as follows: (A): reconstituted control serum, (B): control serum containing 25 mM $CO_3^{2-}$, (C): control serum containing 25 mM $CO_3^{2-}$ and 0.01 mM salicylate, (D): control serum containing 25 mM $CO_3^{2-}$ and 0.1 mM salicylate, (E): control serum containing 25 mM $CO_3^{2-}$ and 1.0 mM $CO_3^{2-}$: (G): control serum containing 25 mM $CO_3^{2-}$; (H) 25 mM $CO_3^{2-}$ in deionized water. Between the measurements, membranes were washed with deionized water, and the serum samples were added in the order shown in the figure.
Figure 6B:
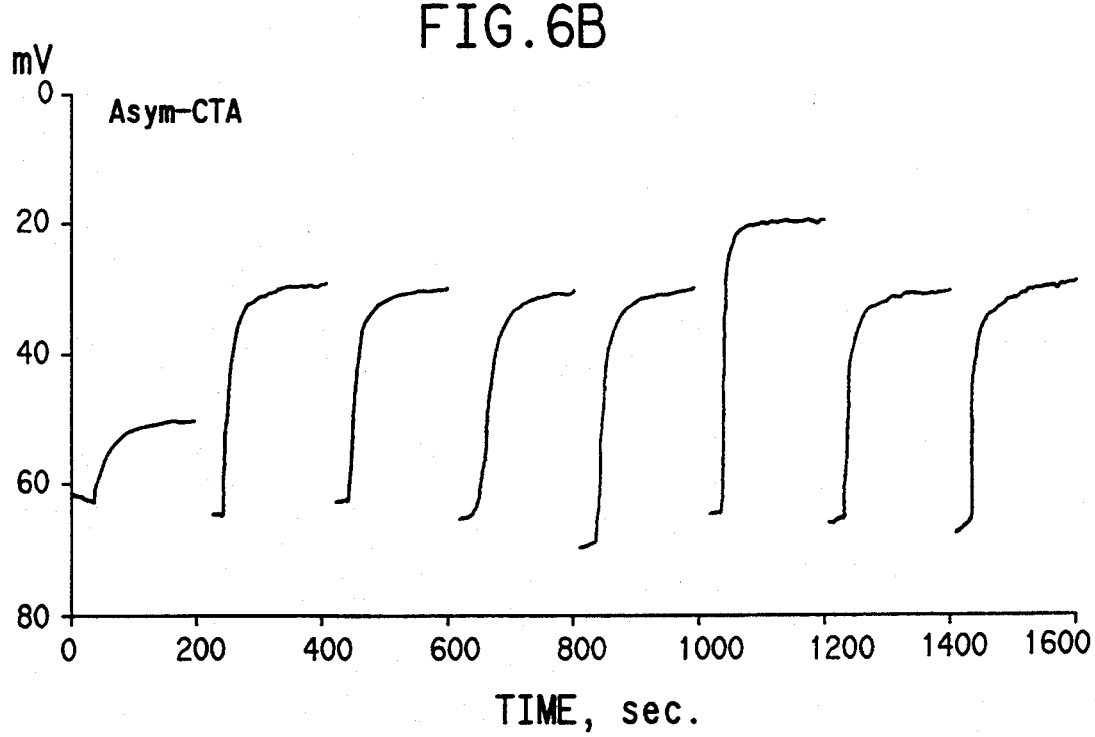
FIG. 6B depicts the potentiometric response of the asymmetric CTA ion selective membrane electrodes to added serum samples containing varying salicylate concentrations as follows: (A): reconstituted control serum, (B): control serum containing 25 mM $CO_3^{2-}$, (C): control serum containing 25 mM $CO_3^{2-}$ and 0.01 mM salicylate, (D): control serum containing 25 mM $CO_3^{2-}$ and 0.1 mM salicylate, (E): control serum containing 25 mM $CO_3^{2-}$ and 1.0 mM $CO_3^{2-}$: (G): control serum containing 25 mM $CO_3^{2-}$; (H) 25 mM $CO_3^{2-}$ in deionized water. Between the measurements, membranes were washed with deionized water, and the serum samples were added in the order shown in the figure.

FIGS. 5A and B show that, unlike the non asymmetric PVC membrane, the asymmetric CTA membrane eliminated the 1.0 mM salicylate interference when used to determine 25 mM carbonate in the presence of 100 mM chloride.

The response differences between the non asymmetric PVC membrane and the asymmetric membrane are further convinced by comparing curve A (response to sample containing 25 mM $CO_{32-}$) with curve C (response to a sample containing 25 mM $CO_{32-}$, 100 mM chloride and 1.0 mM salicylate) of FIGS. 5A and B.

Samples having a serum matrix were tested using the Seramchem Level 1 Clinical Chemistry Control Human Serum Assayed.measurement apparatus. The membranes were washed thoroughly between samples with deionized water and samples were added in the order shown in FIGS. 6A and B.

Curve A (FIGS. 6A and B) was obtained by adding 2 ml of control serum to 18 ml of background buffer in order to determine the amount of carbonate initially present in the reconstituted control serum. The PVC non-asymmetric and asymmetric CTA membranes showed different amounts of $CO_{32-}$, the PVC membrane yielding the higher level signal. The initial amount of $CO_{32-}$ present was determined from the response from the asymmetric CTA membrane since it was known that the PVC membrane suffered from interferences from organic acids. Sodium bicarbonate was added to adjust the reconstituted serum pool to a final $CO_{32-}$ concentration of 25 mM. For the study, reported in FIGS. 6A and B, the required amount of sodium bicarbonate was added to a mixed reconstituted control serum samples (from five 5.0 ml bottles) to make a final total carbonate concentration of 25 mM. Portions (5 ml) of this serum were then spiked with varying amounts of salicylate by adding varying amounts of salicylate to make final salicylate concentrations of 0.01, 0.1 and 1.0 mM respectively. The response of the non-asymmetric PVC and asymmetric CTA membranes to the serum samples were compared by using the high impedance electrometer referred to in Example 2. All tests were performed at room temperature and the EMF values were recorded every 1 second. The electrodes were washed with deionized water between measurements. The tests were duplicated and the results were found to be reproducible.

EXAMPLE 6

Preparation and Use of an Asymmetric Chloride Ion-Selective Membrane

The asymmetric CTA membrane is prepared using the same procedure described above in Example 1.

A 22 mm glass ring is placed on the upper unmodified surface of the polymer membrane and 1.2 ml of methylene chloride (1.2 mL) is confined within the ring.for preconditioning the asymmetric membrane for fusing to the ion selective CTA layer. The entire assembly is placed in a desiccator for approximately 30 minutes, to reduce the rate of evaporation of methylene chloride. The polymer layer having a hydrophilic side is now ready for casting of the ion selective layer.

A solution of the chloride asymmetric ion selective layer components is prepared using a mixed solvent solution of 0.8 ml of methylene chloride and 0.8 ml chloroform containing 35 mg CTA; 100 μL of a mixture containing Aliquat 336 (Aldrich) (5–100% Aliquat 336 can be used; 75% is preferred), preferably and the plasticizer bis (2-ethylhexyl) adipate (Fluka) (95%–0% plasticizer can be used; 25% is preferred) is placed on the upper unmodified (not hydrolyzed) surface of the previously prepared polymer layer in the 22 mm. ring. The entire assembly is then placed in a vacuum desiccator overnight with the tap only slightly opened to control evaporation. In this manner, the polymer layer having a hydrophilic side and the ion selective layers are fused into a single, asymmetric membrane.

The electrochemical properties of this membrane are evaluated using conventual ion-selective electrode membrane holding devices, such as the Phillips electrode body (Glasblaserei Moller, Model IS-561, Zurich, CH). Small 5.5 mm dia disks are punched from the asymmetric CTA membrane as prepared above and placed in the electrode body with the hydrophilic layer facing the sample solution. The inner filling solution is 0.1 M/L NaCl (Baker). The response of the membrane is obtained by using a high input electrometer to measure the potential difference between the sensor electrode and an external sleeve-type double junction silver/silver chloride electrode (Orion, Model 90-02) using 1 M/L KNO3 as an external salt bridge. The potential difference is recorded using an analog-to digital converter and a IBM Personal computer.

Aqueous and serum samples are diluted 1:10 with a tris sulfate buffer pH 8.5. The responses are tested using normal, abnormal, low, and high chloride solutions and compared with the same solution spikes with salicylate as an interfering substance.

EXAMPLE 7

Preparation and Evaluation of an Asymmetric Cellulose Triacetate Chloride Ion-Selective Membrane A thin cellulose triacetate membrane was prepared by dissolving 100 mg of cellulose triacetate (CTA), (Fluka Chemicals, Ronkonkoma, N.Y.) in 2.5 milliliters (ml) of a mixed analytical-reagent grade, solvent containing 1.5 ml of methylene chloride (Junsei Chemical Co., Ltd, Tokyo, Japan) and 1.0 ml of chloroform (Junsei Chemical Co., Ltd, Tokyo, Japan). The solution was cast on a flat plate. Spreading of the solution was confined by a 36 millimeter (mm) inside diameter ring. The solvent was allowed to evaporate overnight leaving a membrane approximately 50 micrometers thick. The acetyl groups on the lower side of the membrane were hydrolyzed by floating the membrane on an excess of 1M (moles/liter) sodium hydroxide (Junsei Chemical Co., Ltd.) solution at room temperature for 7 h. This resulted in a polymeric membrane having a thin hydrophilic, hydroxylated side. The membrane was washed by immersing it in 500 ml of distilled water. This process was repeated a second time to insure termination of the hydrolysis reaction and allowed to air dry at room temperature. The dry membrane was placed on a second glass plate with the hydroxylated, hydrophilic side facing down. A 22 mm inside diameter ring was placed on the upper surface of the membrane to confine the spreading of subsequent solutions. 1.2 ml of methylene chloride was applied to the membrane to soften or pretreat the upper surface for 30 minutes (min). During this period the membrane was kept inside a desiccator with its vacuum tap open to reduce the rate of evaporation of the methylene chloride. A solution of the components for the chloride ion-selective membrane was prepared by dissolving 2.0 mg of the metalloporphyrin ionophore (i.e., chloro(5,10,15,20-tetraphenylporphyrinato)manganese (III) (Mn [TPP]Cl) or chloro (octaethylporphyrinato)indium (III) (In [OEP]Cl)); 35 mg of CTA; and 132 mg of the plasticizing agent, 2-nitrophenyl octyl ether (Fluka Chemicals, Ronkonkoma, N.Y.) in a mixed solvent containing 0.8 ml of methylene chloride and 0.8 ml of chloroform. Mn[TPP]Cl was purchased from Aldrich Chemical Co., Milwaukee, Wis., In[OEP]Cl, synthesized according to a method published by Bhatti, M., Bhatti, W. and Mast, E., "Preparation of Indium(III) Tetraphenylporphine Complexes" Inorg. Nucl. Chem. Lett., vol. 8, pp. 133–137 (1972), was a gift from Professor Mark E. Meyerhoff, Department of Chemistry, University of Michigan, Ann Arbor, Mich., (octaethylporphyrin (Midcentury, Posen, Ill.) can be metallated with In(III) by a known procedure). This solution was applied to the membrane area within the 22 mm diameter ring and allowed to evaporate overnight. Evaporation was controlled by keeping the membrane in a vacuum desiccator with the vacuum tap slightly open. The mixture of the polymer containing the ionophore and plasticizing agent was thereby fused to the nonhydrophilic side of the polymeric membrane to produce an asymmetric chloride ion-selective membrane.

Electrochemical properties of the membranes were evaluated in conventional ion-selective electrode devices. The internal filling solution employed contained 0.1M sodium dihydrogen phosphate, 0.1M disodium hydrogen phosphate, and 0.01M sodium chloride. Potential data were obtained by using the high impedance amplifier/analog-to-digital converter setup described previously.

The potentiometric response characteristics of the asymmetric CTA membranes were evaluated and compared with unmodified CTA membranes. These responses were obtained by adding standard solutions added to a stirred 200 ml volume of background electrolyte (a solution containing 10 mM sodium dihydrogen phosphate, 6.7 mM citric acid and 11.4 mM boric acid, buffered with NaOH to pH 5.5). The results are shown in FIGS. 9A–12B.

Figure 9A:
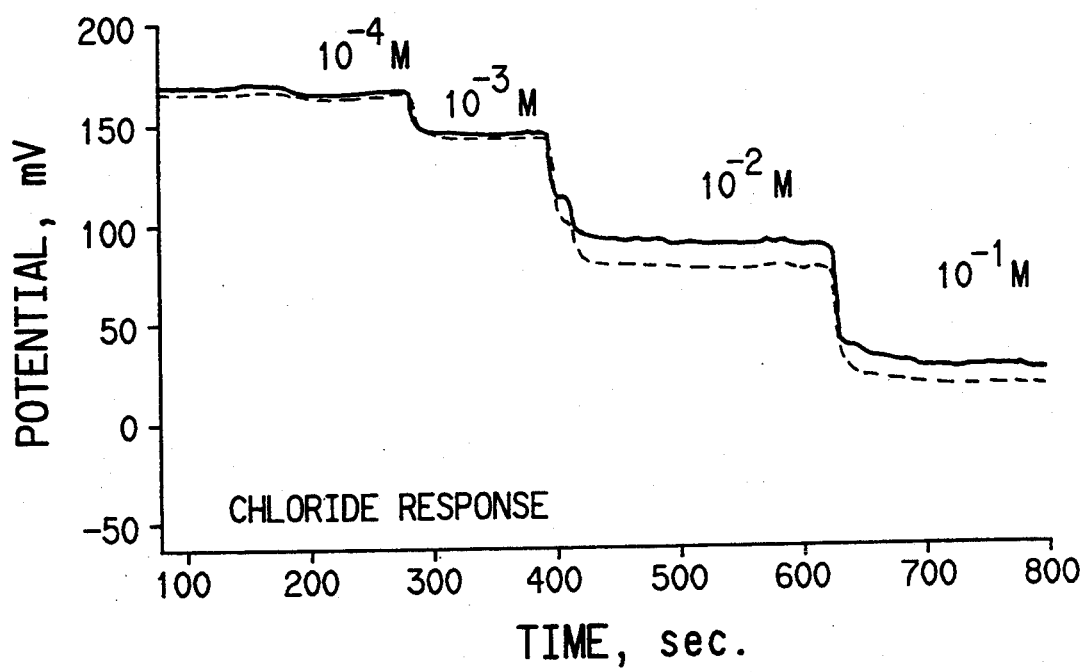
FIG. 9A depicts the dynamic response of an unmodified, normal CTA chloride ion-selective electrode (solid line) and an asymmetric CTA (dotted line) chloride ion-selective membrane electrodes doped with Mn[TPP]Cl on chloride.
Figure 9B:
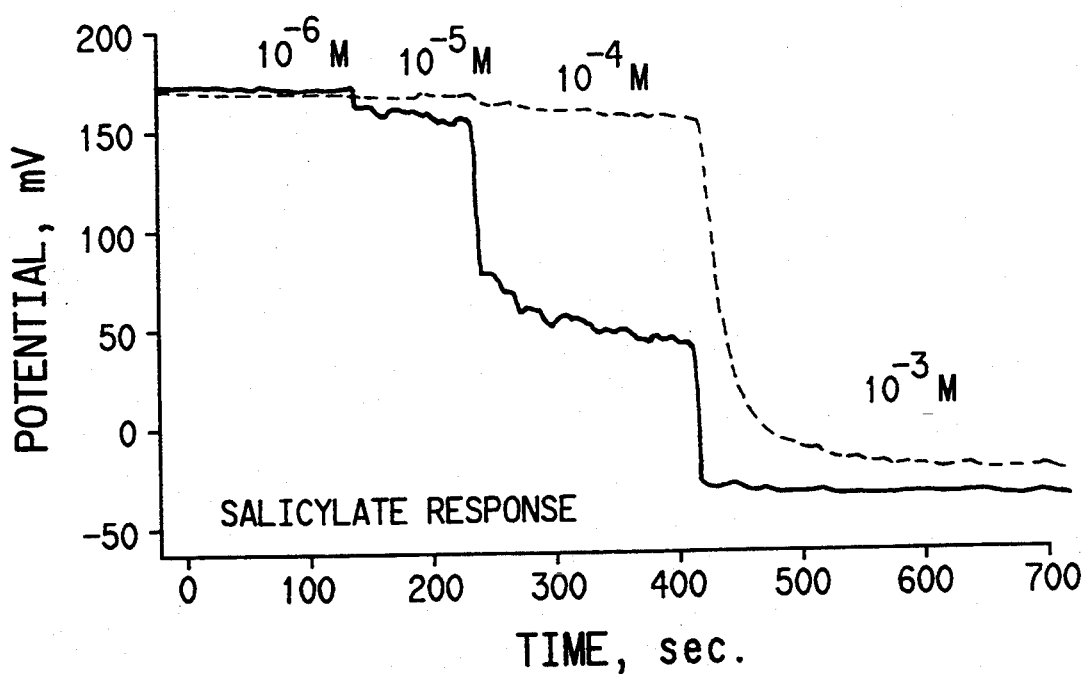
FIG. 9B depicts the dynamic response of an unmodified, normal CTA (solid line) chloride ion-selective electrode and an asymmetric CTA (dotted line) chloride ion-selective membrane electrode doped with Mn[TPP]Cl on salicylate.
Figure 10A:
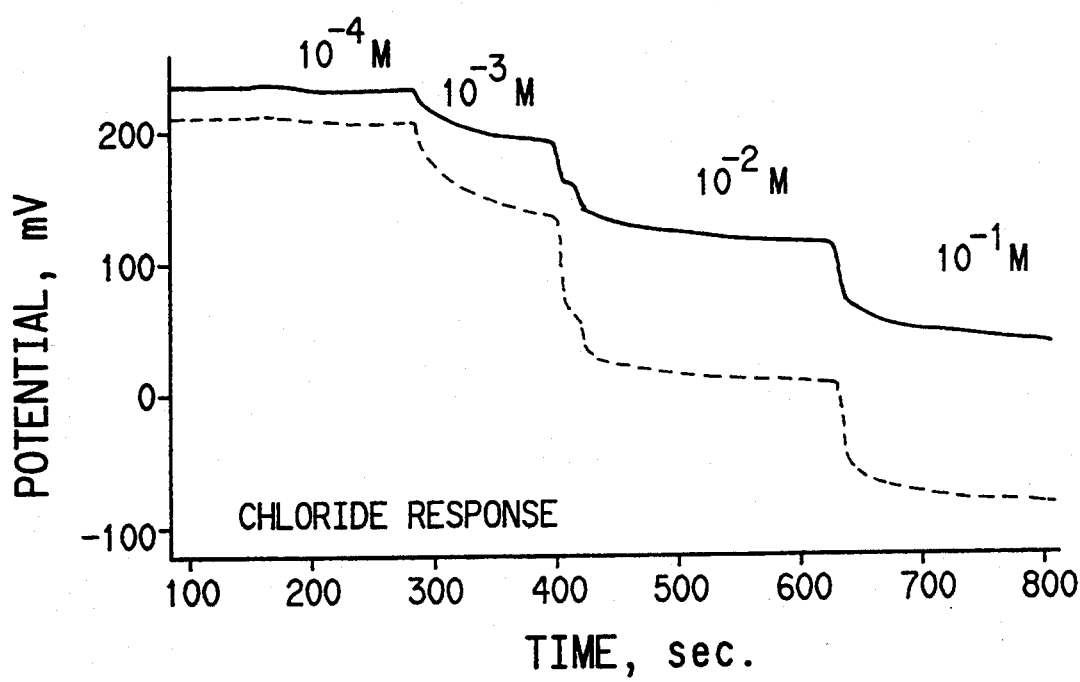
FIG. 10A depicts the dynamic response of an unmodified normal CTA (solid line) chloride ion-selective electrode and an asymmetric CTA (dotted line) chloride ion-selective membrane electrode doped with In[OEP]Cl on chloride.
Figure 10B:
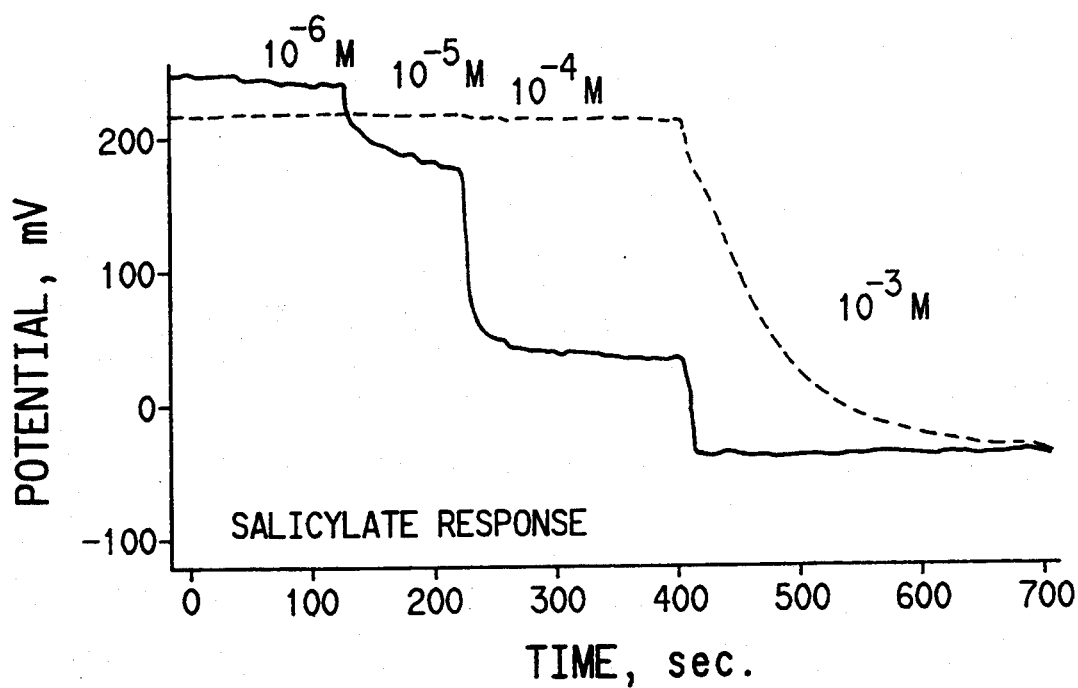
FIG. 10B depicts the dynamic response of an unmodified normal CTA (solid line) chloride ion-selective electrode and an asymmetric CTA (dotted line) chloride ion-selective membrane electrodes doped with In[OEP]Cl on salicylate.
Figure 11A:
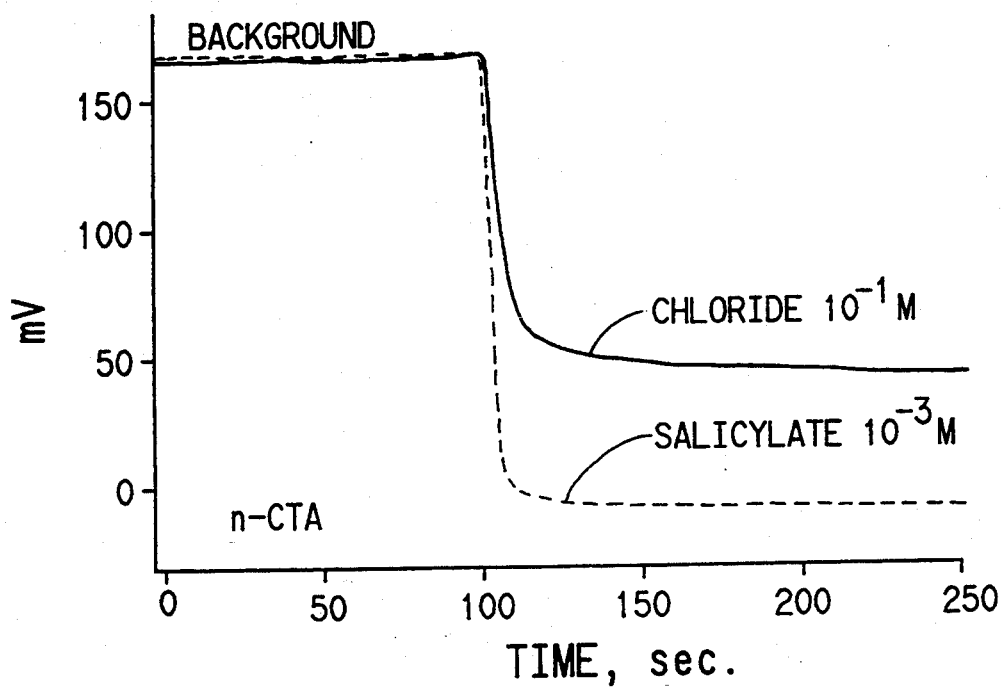
FIG. 11A depicts the dynamic response of unmodified, normal CTA (solid line) chloride ion-selective membrane electrode on chloride and salicylate.
Figure 11B:
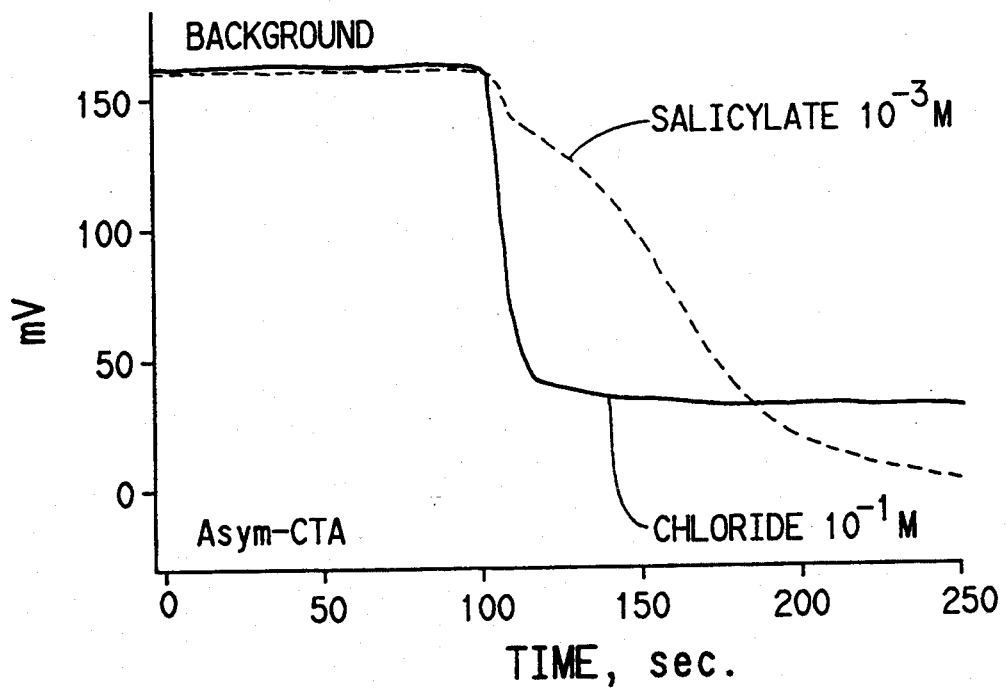
FIG. 11B depicts the dynamic response of an asymmetric CTA chloride selective membrane electrode doped with Mn[TPP]Cl on chloride and salicylate.
Figure 12A:
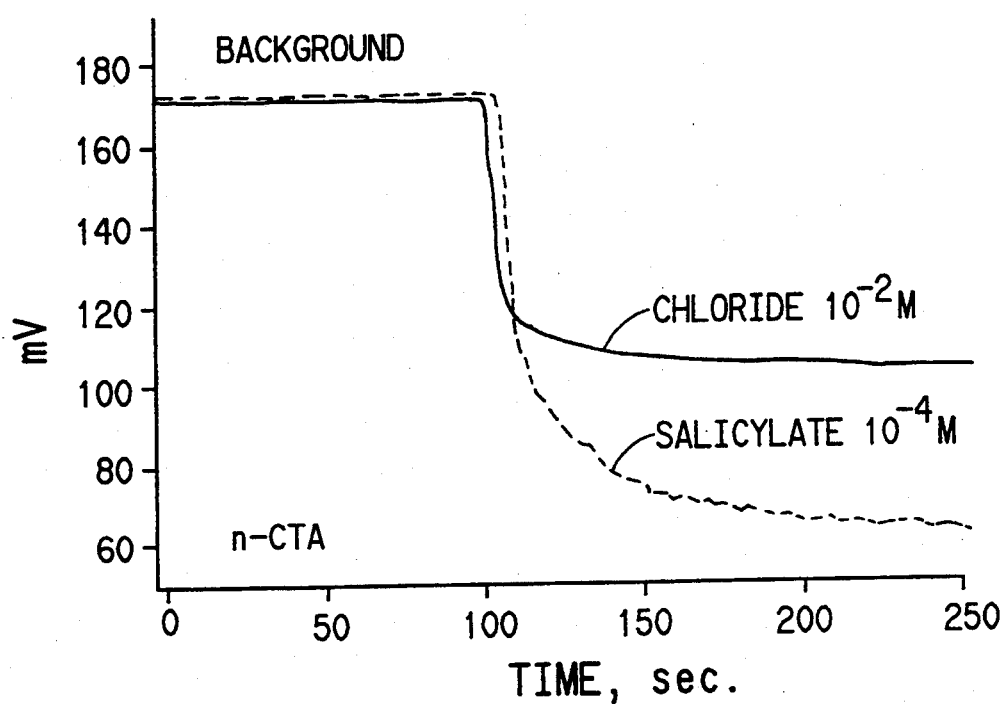
FIG. 12A depicts the dynamic response of an unmodified, normal CTA (solid lines) chloride ion-selective membrane electrode on chloride and salicylate.
Figure 12B:
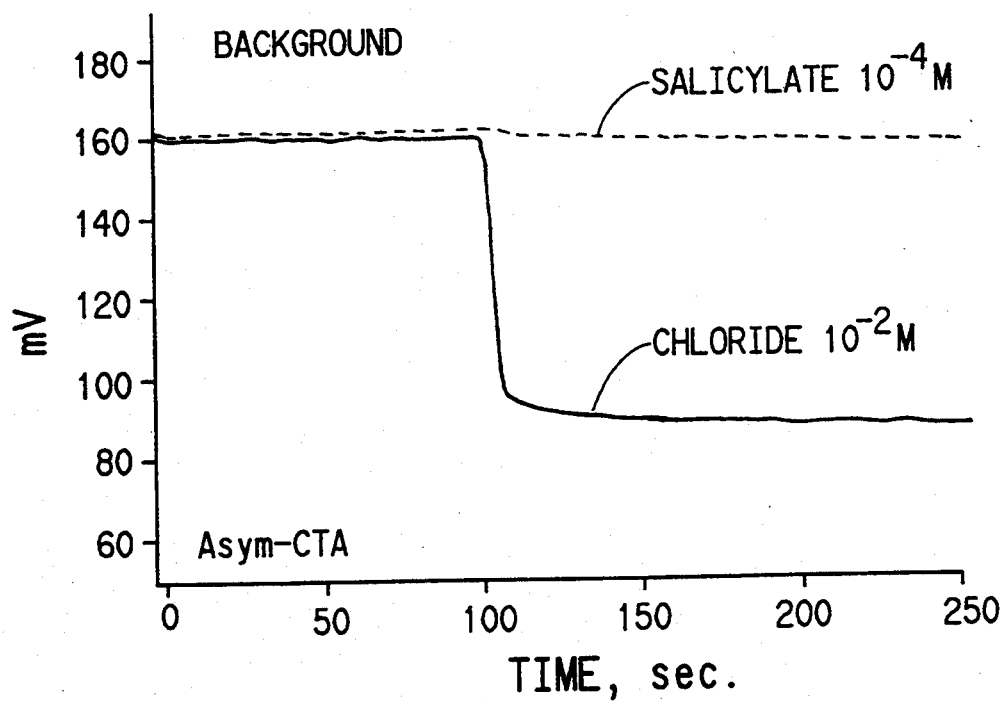
FIG. 12B depicts the dynamic response of an asymmetric CTA chloride ion-selective membrane electrode doped with Mn[TPP]Cl on chloride and salicylate.

FIG. 9A shows the asymmetric chloride membrane electrode having an asymmetric membrane containing the ion-selective agent Mn[TPP]Cl performed comparably to the unmodified chloride selective electrode in responding to varying concentrations of $Cl^-$. FIG. 9B shows the asymmetric chloride membrane electrode (Mn[TPP]Cl) performed substantially better than the unmodified, normal chloride selective membrane electrode in response to salicylate (i.e., reduced salicylate interference). FIGS. 10 and 10B show similar results obtained with the asymmetric chloride membrane electrode having an asymmetric membrane containing the ion-selective agent In[OEP]Cl. FIG. 11A shows the response of unmodified normal CTA chloride selective electrodes on chloride and salicylate. A comparison with 11B shows the asymmetric chloride selective membrane electrode having an asymmetric membrane containing Mn[TPP]Cl performed substantially better than the unmodified CTA chloride selective electrode in response to salicylate (i.e., reduced salicylate interference). FIGS. 12A and 12B show similar results obtained with the asymmetric chloride membrane electrode having an asymmetric membrane containing the ion-selective agent In[OEP]Cl.

What is claimed is:

1. A method of using a potentiometric, ion-selective, asymmetric membrane electrode to enhance potentiometric ion selectivity and to decrease interferences from an interfering ion of interest selected from the group consisting of $Cl^-$, $CO_3^{2-}$, $Li^+$, $Br^-$, $HPO_3^-$ during the assay of a sample, the method comprising:
   (a) contacting a biological sample with the asymmetric, ion-selective electrode membrane which is in contact with a conductor, the asymmetric membrane comprising 1) an ion-selective agent and a plasticizing agent and 2) a hydrophilic layer fused to the ion-selective layer;
   (b) measuring the potential difference between the ion-selective, asymmetric membrane electrode and a reference electrode electrolytically connected to the ion-selective asymmetric membrane electrode in a non-equilibrium or an equilibrium mode; and
   (c) relating the potential difference to the concentration of the ion chosen in the sample, thereby enhancing potentiometric ion selectivity.

2. The process of claim 1 wherein the potential difference is measured kinetically.

3. The process of claim 1 wherein prior to step (a) the biological sample is diluted.

4. The process of claim 1 wherein the conductor is selected from the group consisting of carbon, metal, and metal/metal salt.

5. The process of claim 1 wherein an electrolyte is in contact with the conductor.

6. The process of claim 1 wherein the hydrophilic layer contains hydroxyl groups.

7. The process of claim 1 wherein the hydrophilic layer is selected from the group consisting of cellulose, cellulose ester, poly(vinyl acetate), polyurethane, cellulose, poly(vinyl butyral), poly(vinyl alcohol), and copolymers of vinyl chloride.

8. The process of claim 1 wherein the ion-selective layer is selected from the group consisting of cellulose, cellulose ester, poly(vinyl acetate), polyurethane, cellulose, poly(vinyl butyral), poly(vinyl alcohol), poly(vinyl chloride), and copolymers of vinyl chloride.

9. The process of claim 1 wherein the ion-selective agent is an ionophore.

10. The process of claim 9 wherein the ionophore is selected from the group consisting of trifluoroacetophenone derivatives.

11. The process of claim 1 wherein the plasticizing agent is selected from the group consisting of bis(2-ethylhexyl) sebacate, bis(2-ethylhexyl)adipate, bis(2-ethyl hexyl)phthalate, dicapryl adipate, dipentyl phthalate, dibutyl sebacate, and 2-nitrophenyloctyl ether.

12. The process of claim 1 wherein the biological sample is selected from the group consisting of serum, urine, cerebrospinal fluid, amniotic fluid, plasma, whole blood, saliva, and tears.

13. The process of claim 1 wherein the biological sample contains an interfering substance.

14. The process of claim 13 wherein the interfering substance is selected from the group consisting of salicylate, para-amino salicylate, gentisate, and a combination thereof.

15. The process of claim 1 wherein the ion-selective agent is an ion-complexing agent.

16. A process of claim 1 wherein the ion-selective agent is selected from the group consisting of metalloporphyrins.

17. A method of using a potentiometric, carbonate ion-selective, assymmetric membrane electrode to enhance potentiometric ion selectivity and to decrease interferences from interfering ions during the assay of a sample, the method comprising:
   (a) diluting a biological sample with an amount of a buffer solution such that the concentration of the an interfering substance is less than about $2 \times 10^{-3}M$ and the pH of the diluted sample is about 7.5 to 9.5;
   (b) contacting the diluted sample of step (a) with the asymmetric, carbonate ion-selective electrode membrane, the asymmetric membrane comprising 1) an ion-selective layer comprising an ionophore, an ion complexing agent, and a plasticizing agent, and 2) a hydrophilic layer fused to the ion-selective layer, the hydrophilic layer is in direct contact with the diluted sample;
   (c) measuring the potential difference between the carbonate ion-selective, asymmetric membrane electrode and a reference electrode electrolytically connected to the ion-selective asymmetric membrane electrode in a non-equilibrium or an equilibrium mode; and
   (d) relating the potential difference to the concentration of the carbonate ion chosen in the sample, thereby enhancing potentiometric ion selectivity.

18. The process of claim 17 wherein the conductor is selected from the group consisting of carbon, metal, and metal/metal salt.

19. The process of claim 17 wherein an electrolyte is in contact with the conductor.

20. The process of claim 17 wherein the interfering substance is selected from the group consisting of salicylate, para-amino salicylate, gentisate, and a combination thereof.

21. The process of claim 17 wherein the hydrophilic layer contains hydroxyl groups.

22. The process of claim 17 wherein the hydrophilic layer is selected from the group consisting of cellulose, cellulose ester, poly(vinyl acetate), polyurethane, cellulose, poly(vinyl butyral), poly(vinyl alcohol), and copolymers of vinyl chloride.

23. The process of claim 17 wherein the ion-selective layer is selected from the group consisting of cellulose, cellulose ester, poly(vinyl acetate), polyurethane, cellulose, poly(vinyl butyral), poly(vinyl alcohol), poly(vinyl chloride), and copolymers of vinyl chloride.

24. The process of claim 17 wherein the plasticizing agent is selected from the group consisting of bis(2-ethylhexyl) sebacate and bis(2-ethylhexyl)adipate, bis(2-ethyl hexyl)phthalate, dicapryl adipate, dipentyl phthalate, dibutyl sebacate, and 2-nitrophenyloctyl ether.

25. The process of claim 17 wherein the biological sample is selected from the group consisting of human serum, urine, cerebrospinal fluid, and amniotic fluid, plasma, whole blood, saliva, and tears.

26. A process of claim 17 wherein the ion-complexing agent is selected from the group consisting of tridodecylmethylammonium chloride, methyltricaprylammonium chloride, tetraoctylammonium bromide, and methyltrioctadecyl ammonium bromide.

27. A process of claim 17 wherein the ionophore selected from the group consisting of trifluoroacetophenone derivatives.

* * * * *